(12) United States Patent
Thoma et al.

(10) Patent No.: US 12,712,081 B2
(45) Date of Patent: Aug. 18, 2026

(54) SYSTEM AND METHOD FOR ASSESSING SEVERITY OF NEUTROPHILIC DERMATOSES WITH VISIBLE SKIN MANIFESTATION

(71) Applicants: Boehringer Ingelheim International GmbH, Ingelheim am Rhein (DE); BI X GmbH, Ingelheim am Rhein (DE)

(72) Inventors: Christian Thoma, Ingelheim am Rhein (DE); Aviva Mazurek, Ridgefield, CT (US); Philipp Schwarz, Ingelheim am Rhein (DE)

(73) Assignees: Boehringer Ingelheim International GmbH, Ingelhrim am Rhein (DE); BI X GmbH, Ingelheim am Rhein (DE)

( * ) Notice: Subject to any disclaimer, the term of this patent is extended or adjusted under 35 U.S.C. 154(b) by 234 days.

(21) Appl. No.: 18/620,745

(22) Filed: Mar. 28, 2024

(65) Prior Publication Data

US 2024/0282450 A1 Aug. 22, 2024

Related U.S. Application Data

(63) Continuation of application No. PCT/EP2022/076262, filed on Sep. 21, 2022.

(Continued)

(51) Int. Cl.

| | |
|---|---|
| ***G16H 50/20*** | (2018.01) |
| ***A61B 5/00*** | (2006.01) |
| ***G06T 7/00*** | (2017.01) |
| ***G06V 10/764*** | (2022.01) |
| ***G06V 10/77*** | (2022.01) |

(Continued)

(52) U.S. Cl.

CPC ........... *G16H 50/20* (2018.01); *A61B 5/0077* (2013.01); *A61B 5/0082* (2013.01); *A61B 5/445* (2013.01); *A61B 5/7267* (2013.01); *A61B 5/7275* (2013.01); *G06T 7/0016* (2013.01); *G06V 10/764* (2022.01); *G06V 10/7715* (2022.01); *G06V 10/82* (2022.01); *G06V 40/10* (2022.01);

(Continued)

(58) Field of Classification Search

None

See application file for complete search history.

(56) References Cited

U.S. PATENT DOCUMENTS

| | | | |
|---|---|---|---|
| 9,023,995 B2 | 5/2015 | Brown et al. | |
| 10,219,736 B2 * | 3/2019 | Davis .................. | A61B 5/6898 |

(Continued)

FOREIGN PATENT DOCUMENTS

| | | |
|---|---|---|
| WO | 2013074569 A1 | 5/2013 |

OTHER PUBLICATIONS

Pal et al. ("Severity Assessment of Psoriatic Plaques Using Deep CNN Based Ordinal Classification", Springer Nature Switzerland AG 2018; or 2.0/Care/Clip/ISIC 2018, LNCS;, 2018, pp. 252-259). Provided by applicant. (Year: 2018).*

(Continued)

*Primary Examiner* — Anand P Bhatnagar

(74) *Attorney, Agent, or Firm* — Brake Hughes Bellermann LLP

(57) ABSTRACT

The present description relates to a computer-implemented system and methods for detecting and assessing the severity of a neutrophilic dermatosis condition with visible skin manifestation in a patient before or after a treatment with an anti-interleukin-36 receptor antibody.

23 Claims, 14 Drawing Sheets

Related U.S. Application Data

(60) Provisional application No. 63/249,204, filed on Sep. 28, 2021.

(51) Int. Cl.
*G06V 10/82* (2022.01)
*G06V 40/10* (2022.01)

(52) U.S. Cl.
CPC ............... *G06T 2207/20081* (2013.01); *G06T 2207/20084* (2013.01); *G06T 2207/30088* (2013.01)

(56) References Cited

U.S. PATENT DOCUMENTS

| | | | | |
|---|---|---|---|---|
| 10,499,845 | B2 * | 12/2019 | Do | A61B 5/7264 |
| 11,894,139 | B1 * | 2/2024 | Van Hooser | G06N 20/10 |
| 12,503,512 | B2 * | 12/2025 | Thoma | C07K 16/2866 |
| 12,569,453 | B2 * | 3/2026 | Kraus | A61K 31/05 |
| 12,573,506 | B2 * | 3/2026 | Nakanishi | G16H 50/20 |
| 2017/0231550 | A1 * | 8/2017 | Do | G06T 7/0012<br>382/128 |
| 2022/0033882 | A1 * | 2/2022 | Cook | G16B 20/20 |
| 2022/0290239 | A1 * | 9/2022 | Baum | C12Q 1/6883 |
| 2023/0115617 | A1 * | 4/2023 | Baum | A61P 17/06<br>424/133.1 |
| 2024/0352137 | A1 * | 10/2024 | Hall | C07K 16/2866 |
| 2024/0409646 | A1 * | 12/2024 | Thoma | C07K 16/2866 |

OTHER PUBLICATIONS

Invitation to Pay Additional Fees for PCT Application No. PCT/EP2022/076262, mailed on Feb. 14, 2023, 21 pages.

L. D. Taylor et al.: “A transgenic mouse that expresses a diversity of human sequence heavy and light chain immunoglobulins,” Nucleic Acids Research, vol. 20, No. 23, 1994, pp. 6287-6295.

Hegde, Parameshwar R., et al., “Comparison of Machine Learning Algorithms for Skin Disease Classification Using Color and Texture Features”, IEEE;, 2018, pp. 1825-1828.

Meienberger, N. , et al., “Observer-Independent Assessment of Psoriasis-Affected Area Using Machine Learning”, jeadv 2020, 34; DOI: 10.1111/JDV.16002;, 2020, pp. 1362-1368.

Pal, Anabik , et al., “Severity Assessment of Psoriatic Plaques Using Deep CNN Based Ordinal Classification”, Springer Nature Switzerland AG 2018; or 2.0/Care/Clip/ISIC 2018, LNCS;, 2018, pp. 252-259.

Pal, Anabik , et al., “Severity Grading of Psoriatic Plaques Using Deep Cnn Based Multi-Task Learning”, 2016 23rd International Conference on Pattern Recognition (ICPR) Cancun Center, Cancun, Mexico;, Dec. 4-8, 2016, pp. 1478-1483.

Peng, Li , et al., “Research on Classification Diagnosis Model of Psoriasisresidual Network”, Digital Chinese Medicine 4 (2021);, 2021, pp. 92-101.

* cited by examiner

• : erythema, pustules or scaling

<table>
<tr><td></td><td>clear</td><td>almost clear</td><td>mild</td><td>moderate</td><td>severe</td></tr>
<tr><td>112a</td><td>0</td><td>1</td><td>2</td><td>3</td><td>4</td></tr>
<tr><td>112b</td><td>0</td><td colspan="2">1</td><td colspan="2">3</td></tr>
</table>

Feature map

| -0.11 | 1 | -0.11 |
|---|---|---|
| -0.55 | 0.11 | -0.33 |
| -0.33 | 0.33 | -0.33 |
| -0.22 | -0.11 | -0.22 |
| -0.33 | -0.33 | -0.33 |

703

Rectify (ReLU) →

Rectified Feature map

| 0 | 1 | 0 |
|---|---|---|
| 0 | 0.11 | 0 |
| 0 | 0.33 | 0 |
| 0 | 0 | 0 |
| 0 | 0 | 0 |

704

SYSTEM AND METHOD FOR ASSESSING SEVERITY OF NEUTROPHILIC DERMATOSES WITH VISIBLE SKIN MANIFESTATION

CROSS-REFERENCE TO RELATED APPLICATION

This application claims priority to, and is a continuation of, PCT/EP2022/076262, filed on Sep. 21, 2022 and entitled "SYSTEM AND METHOD FOR ASSESSING SEVERITY OF NEUTROPHILIC DERMATOSES WITH VISIBLE SKIN MANIFESTATION," which in turn claims priority to U.S. Provisional Application No. 63/249,204 filed on Sep. 28, 2021, both of which are hereby incorporated by reference in their entireties.

TECHNICAL FIELD

The present description relates to a computer system and computer-implemented methods for assessing (predicting) the severity of a neutrophilic dermatosis (ND) condition of a patient before or after a treatment with an anti-interleukin-36 receptor (anti-IL-36R) antibody. More specifically, the description relates to a computer-implemented system and method for predicting the severity of generalized pustular psoriasis (GPP) or palmoplantar pustulosis (PPP) of a patient before or after a treatment with Spesolimab (BI 655130).

BACKGROUND

Neutrophilic dermatoses form a heterogeneous group of inflammatory skin disorders that present unique clinical features but are unified by the presence of a sterile, predominantly neutrophilic infiltrate on histopathology. The morphology of cutaneous lesions associated with these disorders is heterogeneous, which renders diagnosis challenging. Moreover, a thorough evaluation is required to exclude diseases that mimic these disorders.

Currently, the diagnosis and the severity assessment of neutrophilic dermatoses are done by licensed dermatologists, who also prescribe treatment regimens based on their subjective diagnosis and assessment.

Unfortunately, manual diagnosis of a neutrophilic dermatosis condition is often subjective and therefore inaccurate. More often, different dermatologists may classify an ND condition at different levels of severity, resulting inconsistent treatment of patients with ND. For example, misclassification of the severity of an ND condition can result in under-treatment, which may prolong the patient's recovery. Similarly, misclassification of the severity of the ND condition can result in overtreatment, causing the patient to be treated with unnecessary amounts of a medicine.

SUMMARY

Therefore, there is the need for a rapid, automatic, and non-subjective method to assess the severity of an ND condition of a patient before or after a treatment wherein the method, which does not rely on a manual diagnosis or assessment of a medical practitioner, supports the medical practitioner in the diagnosis. A patient as used herein refers to a human or a non-human animal that has developed one or more symptoms of a neutrophilic dermatosis, e.g., neutrophilic infiltration in affected skin tissues, pustules, etc., and/or that has been diagnosed with a neutrophilic dermatosis condition with visible skin symptoms including erythema, pustules and/or scaling.

The present description addresses the above need by providing computer system and computer-implemented methods as depicted by the independent claims for automatically evaluating the severity of ND conditions of a patient regarding GPP or PPP, before or after a treatment with a therapeutically effective amount of an anti-IL-36R antibody. In other words, the herein disclosed methods can automatically evaluate the severity of skin lesions in a patient with ND (particularly NDs that have visible signs and symptoms such as skin erythema, pustules and/or scaling), and can assist the treating physician to rapidly and conveniently form an objective assessment of the disease severity for the patient that is needed for an effective treatment.

Definitions

A phrase such as "an aspect" does not imply that such aspect is essential to the present description or that such aspect applies to all configurations of the subject technology. A disclosure relating to an aspect may apply to one or more configurations. An aspect may provide one or more examples of the disclosure. A phrase such as "an embodiment" does not imply that such embodiment is essential to the subject technology or that such embodiment applies to all configurations of the subject technology. Embodiments can also include optional features. A disclosure relating to an embodiment may also apply to higher ranking embodiments. An embodiment may provide one or more examples of the disclosure.

The term "about" shall generally mean an acceptable degree of error or variation for the quantity measured given the nature or precision of the measurements. Typical, exemplary degrees of error or variation are within 5% or within 3% or within 1% of a given value or range of values. For example, the expression of "about 100" includes 105 and 95 or 103 and 97 or 101 and 99, and all values in between (e.g., 95.1, 95.2, etc. for range of 95-105; or 97.1, 97.2, etc. for the range of 97-103; 99.1, 99.2, etc. for the range of 99-101). Numerical quantities given herein are approximates unless stated otherwise, meaning that the term "about" can be inferred when not expressly stated.

A "pharmaceutical composition" refers in this context to a liquid or powder preparation which is in such form as to permit the biological activity of the active ingredient(s) to be unequivocally effective, and which contains no additional components which are significantly toxic to the patients to which the composition would be administered. Such compositions are sterile.

The term "patient" for purposes of treatment refers to any animal classified as a mammal, including humans, domesticated and farm animals, and zoo, sports, or pet animals, such as dogs, horses, cats, cows, and the like, that has developed one or more symptoms of a neutrophilic dermatosis. Preferably, the mammal is human.

As used herein, the terms "treat", "treating", or the like, mean to alleviate symptoms, eliminate the causation of symptoms either on a temporary or permanent basis, or to prevent or slow the appearance of symptoms of the named disorder or condition. These terms are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury, whether or not the treatment leads to amelioration of the disease, comprises "treatment" or "therapy" as used herein. Moreover, as long as the compositions of the description either alone or in combination with another therapeutic agent alleviate or ameliorate at least one symptom of a disorder being treated as compared to that symptom in the absence of use of the humanized anti-IL-36R antibody composition, the result should be considered an effective treatment of the underlying disorder regardless of whether all the symptoms of the disorder are alleviated or not.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression.

As used herein, the terms "skin lesion" refers to a skin area in a patient with ND, which exhibits visible skin manifestation or signs and symptoms including erythema, pustules and/or scaling.

Although any methods and materials similar or equivalent to those described herein can be used in the practice of the present description, the preferred methods and materials are now described. All publications mentioned herein are incorporated herein by reference to describe in their entirety.

Neutrophilic dermatoses (NDs) are a heterogeneous group of conditions that have common features and overlapping pathophysiology. Neutrophilic dermatoses include generalized pustular psoriasis (GPP), palmoplantar pustulosis (PPP), hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DIRTA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis; ostcitis (SAPHO) syndrome; rheumatoid neutrophilic dermatitis (RND), and ichthyosis (and its subtypes including netherton syndrome or NS).

For example, hidradenitis suppurativa (HS) is an inflammatory disease characterized by recurrent, painful abscesses and fistulous tracts. Patients with HS objectively have one of the lowest quality of life measures of any dermatologic disease. Lesions characteristically occur in the axillary, groin, infra-mammary, and/or anogenital regions of the body. HS lesions may progress to form sinus tracts and expansive abscesses.

IL36R is a novel member of the IL1R family that forms a heterodimeric complex with the IL1R accessory protein (IL1RAcp) and IL1Rrp2 associated with epithelial mediated inflammation and barrier dysfunction. The heterodimeric IL36R system with stimulating (IL36α, IL36β, IL36γ) and inhibitory ligands (IL36Ra and IL38) shares a number of structural and functional similarities to other members of the IL1/ILR family, such as IL1, IL18 and IL33. All IL1 family members (IL1α, IL1β, IL18, IL36α, IL36β, IL36γ, and IL38) signal through a unique, cognate receptor protein which, upon ligand binding, recruits the common IL1RAcP subunit and activates NFγB and MAP kinase pathways in receptor-positive cell types (Dinarello, 2011; Towne et al., 2004; Towne et al., 2011). Genetic human studies have established a strong link between IL36R signaling and skin inflammation as demonstrated by occurrence of generalized pustular psoriasis in patients with a loss of function mutation in IL36Ra which results in uncontrolled IL36R signaling (Marrakchi et al., 2011).

Given the strong connection between the IL36 pathway and neutrophilic dermatoses, without wishing to be bound by this theory, it is believed that IL36R biology contributes to pathophysiology of these conditions and hence blocking IL36R activation will be beneficial in patients suffering from a neutrophilic dermatosis. However, an objective evaluation of disease severity in patients with ND is important for a timely and an effective treatment.

Antibodies of the Present Description

The term "antibody," as used herein, includes immunoglobulin molecules comprising four polypeptide chains, two heavy (H) chains and two light (L) chains interconnected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the description, the FRs of the anti-IL-36R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

The antibodies used in the methods of the present description may be human antibodies. The term "human antibody," as used herein, is intended to include antibodies having variable and constant regions derived from human germline immunoglobulin sequences. The human antibodies of the description may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present description may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present description specifically bind IL-36R. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-36R, as used in the context of the present description, includes antibodies that bind IL-36R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-36R may, however, have cross-reactivity to other antigens, such as IL-36R molecules from other (non-human) species.

In certain exemplary embodiments related to any aspects of the present description, the anti-IL-36R antibody or antigen-binding fragment thereof that can be used in the context of the methods of the present description includes: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 or 141 (H-CDR1); the amino acid sequence of SEQ ID NO: 62, 108, 109, 110, 111 or 142 (H-CDR2); the amino acid sequence of SEQ ID NO: 72 (H-CDR3).

Embodiments

In a first aspect, a computer-implemented method is provided for predicting severity of a palmoplantar pustulosis condition of a patient using a deep neural network model. Predicting such a severity level (severity score) using a deep neural network means that the neural network implements a classifier which is suitable to classify the patient's condition in accordance with a classification scheme which was learned by the neural network in a training phase based on appropriate training data. In general, the term "predict" as used herein is used in its commonly known meaning in the context of classification tasks performed by neural networks. In this context, a respectively trained neural network classification model returns predicted class labels in response to a test input provided to the neural network. That is, the term "predict" is to be understood as classifying a current test input and not in the sense that a future medical state of the patient is predicted. In the context of this document, a test input is classified into severity scores which reflect the severity level of the patient's current ND condition. In other words, the prediction/classification corresponds to an assessment of the patient's ND condition in accordance with the test input.

The computer system executing the computer-implemented method receives a test input being a digital image showing skin areas of the patient. The computer system receives the digital image via an appropriate interface. A patient suffering from PPP typically shows erythema, pustules and/or scaling symptoms on the skin of characteristic body parts which are typically affected by PPP. For PPP, such characteristic body parts comprise left and right palm and left and right sole of the patient. The skilled person understands that in case of an animal palms and soles may correspond to respective paws of the animal. The test input digital image comprises a grid with at least one pair of tiles. Advantageously, the tiles are of the same size, with the first tile showing a skin area of the front of a characteristic body part of the patient, and the second tile showing a skin area of the back of the characteristic body part of the patient. For a patient suffering from PPP, at least one of the skin areas exhibits at least one of erythema, pustules, and scaling on the skin. For example, the pair of tiles may include two images showing the front and back of the patient's right palm. A second pair of tiles may be included in the grid showing the front and back of the patient's left palm. Further, rows of the grid may include further pairs of tiles associated with the patient's left and/or right sole. The sub-images in each tile may be captured by using a digital camera. The image grid may be composed from single images showing either the back or front of the respective body part. Such image composition into the final image grid can be performed by the digital camera or by a pre-processing step which combines single images into a corresponding image grid. That is, the tiles of the input image grid show sub-images of the characteristic body parts of the same patient captured within a relatively short time interval so that all tiles reflect the same medical state of said patient.

In a further step, the computer system uses a predictor module with a deep neural network model to predict a total palmoplantar pustulosis global assessment (PPPGA) score for the patient. Thereby, the received image grid serves as input to the deep neural network model (DNN). The DNN has been trained previously with a training data set comprising a plurality of training images having the same structure as the test input. That is, the training images include the same number of tiles showing the same characteristic body parts of test patients in the same order as the test input image. The images were captured from a plurality of test patients selected in accordance with predefined inclusion/exclusion criteria which ensure that the training patients have a generalized pustular psoriasis without history conflicting diseases. The inclusion/exclusion criteria are described in detail in the detailed description. The training data set comprises multiple training images of each test patient captured at different time points during a predefined minimum time interval. Each training image is annotated with one or more severity scores associated with erythema, pustules and scaling as the ground truth reflecting the severity of the palmoplantar pustulosis condition of the respective training patient at the timepoint the training image was captured. In other words, a training image may have a single annotation for an overall severity score for the training patient as ground truth which reflects already a total severity score taking into account all of the PPP symptoms. Alternatively, the training image may be annotated with individual severity scores for each of the erythema, pustules and scaling symptoms. Based on such individual severity scores a total severity score for said patient is finally determined by the predictor. For assessing severity of ND conditions, the training images do not need to include images of healthy patients. Nevertheless, some of the selected training patients may not show any visible sign of erythema, pustules or scaling. However, there is also no restriction with regard to also using healthy patients as training patients.

In a second aspect, a computer-implemented method is provided for predicting severity of a generalized pustular psoriasis condition of a patient using a deep neural network model. The architecture of the deep neural network model is the same as for the first aspect. However, there is a difference in the received test input and the corresponding training data used in the second aspect. In the second aspect, the characteristic body part shown on the test input is selected from: trunk, left and right lower limb, left and right upper limb. To process the test input of the second aspect, the deep neural network model has been trained previously with a training data set which includes training images having the same structure as the test input and captured from test patients in accordance with predefined inclusion/exclusion criteria which ensure that the training patients have a generalized pustular psoriasis history without conflicting diseases. Again, the training data set comprises multiple training images of each test patient captured at different time points during a predefined minimum time interval, and each training image is annotated with one or more severity scores associated with erythema, pustules and scaling as the ground truth reflecting the severity of the generalized pustular psoriasis condition of the respective training patient at the timepoint the training image was captured. Once the DNN has been trained accordingly, it predicts a total Generalized Pustular Psoriasis Physician Global Assessment (GPPGA) score for the patient based on the received test input.

The following optional features can be used for the computer-implemented methods according to the first and second aspects.

In one implementation, the training images can be annotated with one of at least three severity score values covering a severity range from clear to severe. A single annotated severity score value may reflect an average of individual erythema, pustules, and scaling severity scores for the respective training image. For this training scenario, the trained deep neural network model provides a single severity score value as output for the test input of said patient.

In an alternative implementation, each training image is annotated with individual erythema, pustules and scaling severity score values. Each individual severity score value is one of at least three severity score values covering a severity range from clear to severe for the respective erythema, pustules and scaling severity on the training image. In this implementation, the trained deep neural network model provides individual severity score values for each of erythema, pustules and scaling severity as outputs. Therefore, the predictor module is configured to determine a single severity score for the test input of said patient based on averaging the determined individual severity score values.

The severity range of the two above implementations may also include more than three severity score values. For example, the following five score values for severity levels may be used clear, almost clear, mild, moderate, and severe with the severity increasing from clear to severe. The severity levels may be implemented using a corresponding five-point scale comprising: 0 if the predicted severity score equals zero, 1 if the predicted severity score is greater than zero but less than 1.5, 2 if the predicted severity score is equal to or greater than 1.5 but less than 2.5, 3 if the predicted severity score is equal to or greater than 2.5 but less than 3.5, and 4 if the predicted severity score is equal to or greater than 3.5. A predicted severity score of ≥2 can be an indicator for administering to the patient a recommended dosage based on a pharmaceutically effective amount of an anti-IL-36R antibody. The five-point scale with the threshold value of "2" is a commonly used scale for the severity assessment. However, other scales may be used as well.

In one embodiment, the present description relates to a method for treating a patient suffering from a neutrophilic dermatosis condition, said method comprising: (a) identifying a skin lesion exhibiting erythema, pustules and/or scaling in the patient, scoring a severity for each erythema, pustules and scaling, and calculating a total neutrophilic dermatosis Global Assessment (NDGA) score or a neutrophilic dermatosis Global Pustules (NDGP) score for the patient, wherein the identifying, scoring and calculating step is a computer-implemented method comprising: (i) providing a digital image of a skin area in the patient, (ii) scoring the severity of the erythema, pustules and/or scaling of the skin lesion on a five-point severity scale of zero to four, wherein the five-point severity scale comprises zero for clear, one for almost clear, two for mild, three for moderate and four for severe; and (iii) calculating the total NDGA score or the NDGP score for the patient on a five-point scale of zero to four, wherein the total NDGA score is the sum of the severity scores for erythema, pustules and scaling obtained in step (ii) divided by three, wherein the NDGP score is the pustules severity score obtained in step (ii), and wherein the five-point scale comprises: 0 if the total NDGA score or the NDGP score equals zero, 1 if the total NDGA score or the NDGP score is greater than zero but less than 1.5, 2 if the total NDGA score or the NDGP score is equal to or greater than 1.5 but less than 2.5, 3 if the total NDGA score or the NDGP score is equal to or greater than 2.5 but less than 3.5, and 4 if the total NDGA score or the NDGP score is equal to or greater than 3.5; and (b) determining if the patient exhibits a score of ≥2 for the total NDGA score or the NDGP score and administering to the patient a recommended dosage based on a pharmaceutically effective amount of an anti-IL-36R antibody for treatment of PPP or GPP, respectively (dependent on the first or second aspect).

For example, the pharmaceutically effective amount of the anti-IL-36R antibody is in the range of about 0.001 to about 1200 mg. In an embodiment, the pharmaceutically effective amount of Spesolimab (BI 655130) is in the range of about 0.001 to about 1200 mg. Therefore, the anti-IL-36R antibody (e.g., Spesolimab (BI 655130)) may be administered to the patient in the range of 0.001 to 1200 mg.

In one embodiment, the severity prediction based on the test input image grid can be further enhanced by combining feature sets of clinical tabular data of the patient with features extracted from respective digital images of the patient for the severity prediction of said patient. Thereby, a particular feature set of clinical tabular data and a respective digital image are associated with the same severity of the patient's condition. In other words, the test input image and the respective clinical tabular data are captured within a given time interval (e.g., on the same day) so that it is ensured that the digital image and the respective clinical tabular data reflect the same severity score for either PPP or GPP (dependent on the test input and corresponding predictor implementation) of said patient.

For this embodiment, again two alternative implementations may be used. In one implementation, the clinical tabular data features are normalized and concatenated to the respective features extracted from the convolutional layers of the deep neural network, and the concatenated feature set is used as input layer of the classification (fully connected) layers of the deep neural network model. The deep neural network in this implementation is being trained with respective enhanced training data comprising the plurality of training images and the associated feature sets of the clinical tabular data. The deep neural network model may implement any of the following algorithms: Convolutional Neural Network (e.g., ResNet, EfficientNet or ConvNEXT architectures), Vision Transformer, and combination network with convolutional layers and attention layers.

In an alternative implementation, the predictor further comprises a clinical data classifier which has been trained on clinical tabular data features associated with the respective training images of the deep neural network model using the same ground truth. That is, if a training image was annotated with a particular severity score the corresponding tabular clinical data feature set is also annotated with the same particular severity score as ground truth. The deep neural network and the clinical data classifier are then trained together by using Ensemble Learning. The clinical data classifier may be based on a different architecture than the DNN. For example, it may be implemented using Logistic regression, Gradient Boosting, Random Forest, or Support Vector Machine. In this alternative implementation, the predictor finally combines the output of the deep neural network model and the output of the clinical data classifier into a single severity score.

In an embodiment, a computer program product is provided for predicting severity of a palmoplantar pustulosis condition in accordance with the first aspect, or a generalized pustular psoriasis condition of a patient in accordance with the second aspect. The computer program product, when loaded into a memory of a computing device and executed by at least one processor of the computing device, causes the at least one processor to execute the steps of the computer-implemented methods as disclosed herein.

In one embodiment, a method is provided for treating a patient suffering from palmoplantar pustulosis. In an initial step, the computer-implemented method in accordance with the first aspect is executed to predict a severity score of a palmoplantar pustulosis condition of the patient. Then, the computer compares the predicted severity score with a predefined drug administering threshold. If the predicted severity score is equal to or greater than the predefined drug administering threshold, the computer determines a recommended dosage based on the pharmaceutically effective amount of an anti-interleukin-36 receptor antibody. Finally, the recommended dosage of the anti-interleukin-36 receptor antibody for treatment of the palmoplantar pustulosis is administered to the patient.

In a further embodiment, a method is provided for treating a patient suffering from generalized pustular psoriasis. In an initial step, the computer-implemented method in accordance with the first aspect is executed to predict a severity score of a generalized pustular psoriasis condition of the patient. Then, the computer compares the predicted severity score with a predefined drug administering threshold. If the predicted severity score is equal to or greater than the predefined drug administering threshold, the computer determines a dosage recommendation based on the pharmaceutically effective amount of an anti-interleukin-36 receptor antibody. Finally, the recommended dosage of the anti-interleukin-36 receptor antibody for treatment of the generalized pustular psoriasis is administered to the patient.

In one embodiment, a computer system is provided for predicting severity of a palmoplantar pustulosis condition (PPP) and/or a generalized pustular psoriasis condition (GPP) of a patient using one or more respectively trained deep neural network models. The computer system may load and execute the above computer program product to perform the computer-implemented steps of the herein disclosed methods.

The computer system comprises an interface configured to receive a test input digital image with skin areas of the patient. For example, the interface may receive the test input via a wireless communication interface or a wired interface (e.g., an interface for data exchange via a local area network). The test input digital image comprises multiple images arranged as tiles in a grid. The grid comprises at least one pair of tiles, wherein the first tile shows a skin area of the front of a characteristic body part of the patient, and the second tile shows a skin area of the back of the characteristic body part of the patient. Advantageously, the tiles of the test input are of the same size. For patients suffering from PPP or GPP, at least one of the skin areas exhibits at least one of erythema, pustules and scaling on the skin. In case the patient is suffering from PPP, the characteristic body part is selected from: left and right palm, left and right sole. In case the patient is suffering from GPP, the characteristic body part is selected from: trunk, left and right lower limb, left and right upper limb. The skilled person is aware that for animal patients the corresponding characteristic body parts may be called differently. The grid image may be directly received from a respective digital camera or from a pre-processing unit which composes the grid image from multiple single images captured by a standard digital camera.

Further, the system has a predictor module to predict a total palmoplantar pustulosis global assessment score and/or a total Generalized Pustular Psoriasis Physician Global Assessment score for the patient (dependent on the type of test input and the training of the DNN). Thereby, the predictor applies the one or more respectively trained deep neural network model(s) to the test input. That is, the test input serves as the input to the DNN(s). The DNN(s) are trained with a corresponding training data set comprising a plurality of training images having the same structure as the test input and being captured from a plurality of test patients (90) selected in accordance with predefined inclusion/exclusion criteria which ensure that the training patients (90) have, respectively, a PPP history and/or GPP history without conflicting diseases.

The training data set comprises multiple training images of each training patient captured at different time points during a predefined minimum time interval, and each training image is annotated with one or more severity scores associated with erythema, pustules and scaling as the ground truth reflecting respectively the severity of the palmoplantar pustulosis condition and/or the generalized pustular psoriasis condition of the respective training patient at the timepoint the training image was captured. In other words, the DNN(s) is trained in a training phase prior to its application to a test input with suitable training data which allow the DNN to classify the severity of the patient's ND condition either for PPP or for GPP. Advantageous DNN topologies for this purpose include, but are not limited to Vision Transformer, combination network stacking convolutional layers and attention layers, and Convolutional Neural Network topologies, such as for example, ResNet, EfficientNet or ConvNeXT architectures.

In an optional embodiment, the predictor module may combine feature sets of clinical tabular data of the patient with features extracted from respective digital images of the patient for the severity prediction of said patient. Thereby, a particular feature set of clinical tabular data and a respective digital image are associated with the same severity of the patient's condition. Advantageously, the capturing of the digital test input image and the corresponding clinical tabular data test input occurs within a given time interval (e.g., during the same day) so that the same ND condition of the patient is reflected by both, the image test input and the tabular data test input.

Two alternative implementations for the optional embodiment are disclosed. In one implementation, the predictor is further configured to normalize the clinical tabular data features and concatenate the normalized features to the respective image features extracted from the convolutional layers (CNN) of the deep neural network. The concatenated feature set is then used as input layer of the classification layers of the DNN. In this implementation, DNN has been trained with respective enhanced training data comprising the plurality of training images and associated feature sets of clinical tabular data features.

In an alternative implementation, the predictor further comprises a clinical data classifier that has been trained on clinical tabular data features associated with the respective training images of the deep neural network model using the same ground truth. The joint training of the clinical data classifier (CDC) and the deep neural network is performed by using so-called Ensemble Learning. Further, predictor is configured to combine the output of the deep neural network model and the output of the clinical data classifier into a single severity score.

In one embodiment, the system further has a severity checker module to compare the predicted severity score with a predefined drug administering threshold. The predicted severity score has one of at least three severity score values covering a severity range from clear to severe. If the predicted severity score is equal to or greater than the predefined drug administering threshold, the severity checker assigns the patient as a candidate for treatment with an anti-interleukin-36 receptor antibody.

In one embodiment, the system further has an antibody dosage module configured to determine for the candidate for treatment, based on the predicted severity score, a dosage recommendation based on a pharmaceutically effective amount of the anti-interleukin-36 receptor antibody suitable for treatment of the palmoplantar pustulosis condition and/or the generalized pustular psoriasis condition of the candidate. The corresponding dosage instructions are provided to a drug administering entity for executing the treatment of the patient.

As mentioned earlier, the herein disclosed description can also be used in methods for treating a patient suffering from a neutrophilic dermatosis condition, such as PPP or GPP.

The disclosed methods and system may also be used by a method of modifying, discontinuing, or continuing the therapy of an individual receiving an anti-IL-36R antibody for treatment of PPP/GPP where the predicted severity score serves as a basis for modifying, discontinuing, or continuing the treatment, or as a basis for characterizing the patient as likely to respond to treatment with the anti-IL-36 antibody.

Further, if the predicted severity score of a patient decreases over time, that is the repeated execution of the methods according to the first and/or second aspects over a certain time interval leads to decreasing severity scores, the patient is characterized as likely to respond to treatment with the anti-IL-36 antibody based on the previously determined severity score(s).

In an embodiment relating to any of the above aspects or embodiments for treatment of a patient with a PPP and/or GPP condition, the anti-IL-36R antibody comprises: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 or 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects or embodiments for treatment of a patient with a PPP and/or GPP condition, the anti-IL-36R antibody comprises: a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects or embodiments for treatment of a patient with a PPP and/or GPP condition, the anti-IL-36R antibody comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

In an embodiment relating to any of the above aspects or embodiments for treatment of a patient with a PPP and/or GPP condition, the anti-IL-36R antibody comprises:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

In an embodiment relating to any of the above aspects or embodiments for treatment of a patient with a PPP and/or GPP condition, the anti-IL-36R antibody comprises:

i. a light chain comprising the amino acid sequence of SEQ ID NO: 115; and a heavy chain comprising the amino acid sequence of SEQ ID NO: 125; or
ii. a light chain comprising the amino acid sequence of SEQ ID NO: 115; and a heavy chain comprising the amino acid sequence of SEQ ID NO: 126; or
iii. a light chain comprising the amino acid sequence of SEQ ID NO: 115; and a heavy chain comprising the amino acid sequence of SEQ ID NO: 127; or
iv. a light chain comprising the amino acid sequence of SEQ ID NO: 118; and a heavy chain comprising the amino acid sequence of SEQ ID NO: 125; or
v. a light chain comprising the amino acid sequence of SEQ ID NO: 118; and a heavy chain comprising the amino acid sequence of SEQ ID NO: 126; or
vi. a light chain comprising the amino acid sequence of SEQ ID NO: 118; and a heavy chain comprising the amino acid sequence of SEQ ID NO: 127; or
vii. a light chain comprising the amino acid sequence of SEQ ID NO: 123; and a heavy chain comprising the amino acid sequence of SEQ ID NO: 138; or
viii. a light chain comprising the amino acid sequence of SEQ ID NO: 123; and a heavy chain comprising the amino acid sequence of SEQ ID NO: 139; or
ix. a light chain comprising the amino acid sequence of SEQ ID NO: 124; and a heavy chain comprising the amino acid sequence of SEQ ID NO: 138.

In an embodiment related to any of the above aspects or embodiments for treatment of a patient with a PPP and/or GPP condition, the anti-IL-36R antibody is Spesolimab (BI 655130).

The herein disclosed methods and systems may also be applied for predicting severity scores of further (related) neutrophilic dermatosis conditions of a patient when adapting the image training data and test inputs to the corresponding disease. Such further neutrophilic dermatosis conditions may include any of the following: hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DIRTA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis; ostcitis (SAPHO) syndrome; rheumatoid neutrophilic dermatitis (RND), and ichthyosis (and its subtypes including netherton syndrome or NS).

In a related embodiment, the neutrophilic dermatosis is hidradenitis suppurativa (HS). In a related embodiment, the neutrophilic dermatosis is acute generalized exanthematous pustulosis. In a related embodiment, the neutrophilic dermatosis is acute febrile neutrophilic dermatosis (Sweet syndrome). In a related embodiment, the neutrophilic dermatosis is amicrobial pustulosis of the folds (APF). In a related embodiment, the neutrophilic dermatosis is Behcet disease. In a related embodiment, the neutrophilic dermatosis is bowel bypass syndrome (bowel-associated dermatitis-arthritis syndrome). In a related embodiment, the neutrophilic dermatosis is bowel-associated dermatosis-arthritis syndrome (BADAS). In a related embodiment, the neutrophilic dermatosis is CARD14-mediated pustular psoriasis (CAMPS). In a related embodiment, the neutrophilic dermatosis is cryopyrin associated periodic syndromes (CAPS). In a related embodiment, the neutrophilic dermatosis is deficiency of interleukin-36 receptor antagonist (DIRTA). In a related embodiment, the neutrophilic dermatosis is deficiency of interleukin-I receptor antagonist (DIRA). In a related embodiment, the neutrophilic dermatosis is erythema elevatum diutinum. In a related embodiment, the neutrophilic dermatosis is Histiocytoid neutrophilic dermatitis. In a related embodiment, the neutrophilic dermatosis is infantile acropustulosis. In a related embodiment, the neutrophilic dermatosis is neutrophilic dermatosis of the dorsal hands. In a related embodiment, the neutrophilic dermatosis is neutrophilic eccrine hidradenitis. In a related embodiment, the neutrophilic dermatosis is neutrophilic urticarial dermatosis. In a related embodiment, the neutrophilic dermatosis is palisading neutrophilic granulomatous dermatitis. In a related embodiment, the neutrophilic dermatosis is plaque psoriasis. In a related embodiment, the neutrophilic dermatosis is pyoderma gangrenosum, acne, and hidradenitis suppurativa (PASH) syndrome. In a related embodiment, the neutrophilic dermatosis is pyoderma gangrenosum (PG). In a related embodiment, the neutrophilic dermatosis is pyoderma gangrenosum and acne (PAPA). In a related embodiment, the neutrophilic dermatosis is pyogenic arthritis. In a related embodiment, the neutrophilic dermatosis is skin lesions of Behcet's disease. In a related embodiment, the neutrophilic dermatosis is Still's disease. In a related embodiment, the neutrophilic dermatosis is subcorneal pustulosis (Sneddon-Wilkinson). In a related embodiment, the neutrophilic dermatosis is synovitis, acne, pustulosis-hyperostosis and ostcitis (SAPHO) syndrome. In a related embodiment, the neutrophilic dermatosis is rheumatoid neutrophilic dermatitis (RND). In a related embodiment, the neutrophilic dermatosis is ichthyosis (and its subtypes including netherton syndrome or NS).

It will be understood that any of the herein disclosed methods, administration schemes and/or dosing regimens also equally apply to the use of any of the disclosed anti-IL-36R antibodies in such methods, administration schemes and/or dosing regimens: i.e., an anti-IL-36R antibody, as disclosed herein, for use in the treatment, prevention, reducing and/or amelioration of any of the disclosed diseases and/or conditions. In other words, the description also provides for the use of an anti-IL-36R antibody, as disclosed herein, for the manufacture of a medicament for the treatment, prevention, reducing and/or amelioration of any of the disclosed diseases and/or conditions.

Additional features and advantages of the description will be realized and attained by means of the elements and combinations particularly depicted in the appended claims or in the detailed description and figures. It is to be understood that both, the foregoing general description and the following detailed description are exemplary and explanatory only and are not restrictive.

DETAILED DESCRIPTION

Before the present description is described, it is to be understood that this description is not limited to particular methods and experimental conditions described, as such methods and conditions may vary. It is also to be understood that the terminology used herein is for the purpose of describing particular embodiments only, and is not intended to be limiting, since the scope of the present description will be limited only by the appended claims.

In the following detailed description, numerous specific details are set forth to provide a full understanding of the present description. It will be apparent, however, to one of ordinarily skilled in the art that the subject technology may be practiced without some of these specific details. In other instances, well-known structures and techniques have not been shown in detail so as not to obscure the present description.

Unless defined otherwise, all technical and scientific terms used herein have the same meaning as commonly understood by one of ordinary skill in the art to which this description belongs.

Figure 1:
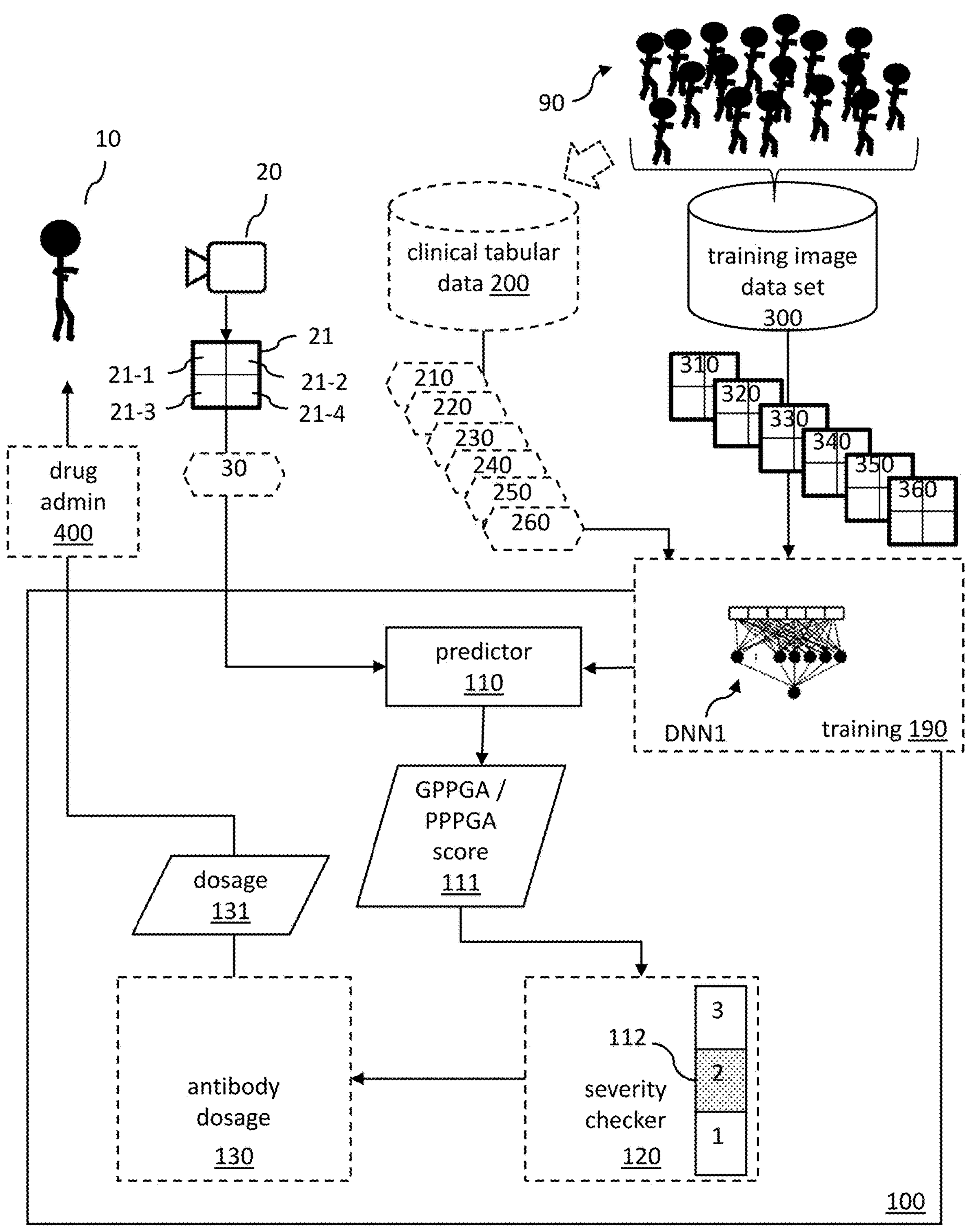
FIG. 1 comprises a simplified block diagram of a computer system for predicting severity of a neutrophilic dermatosis condition of a patient according to an embodiment.
Figure 2A:
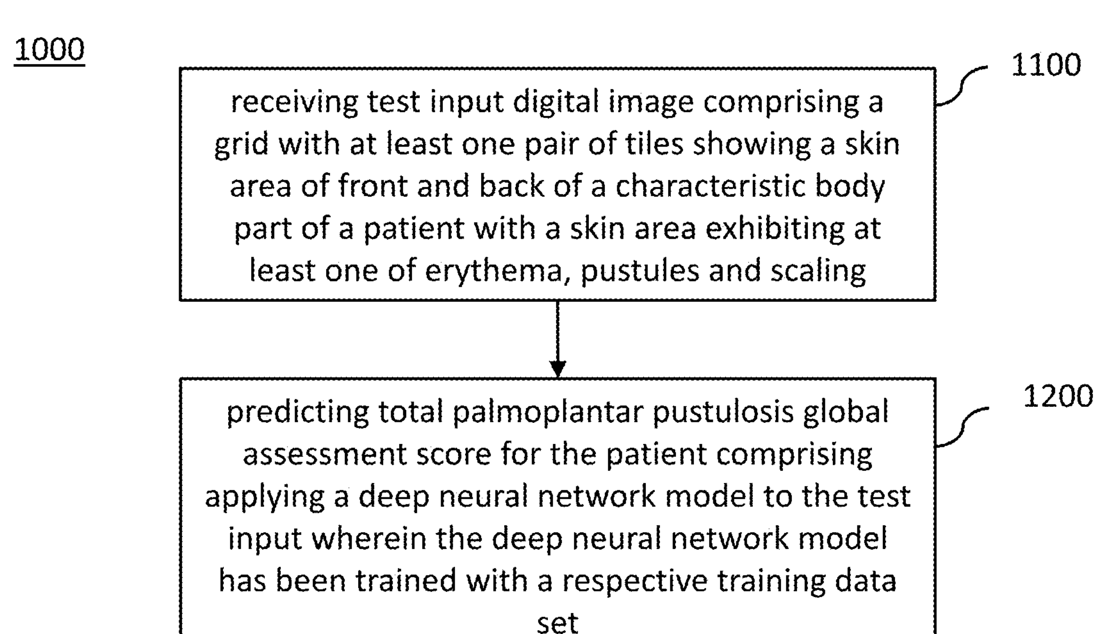
FIGS. 2A, 2B are simplified flowcharts of computer-implemented methods for predicting severity of PPP/GPP conditions of a patient in accordance with two aspects of the description.
Figure 2B:
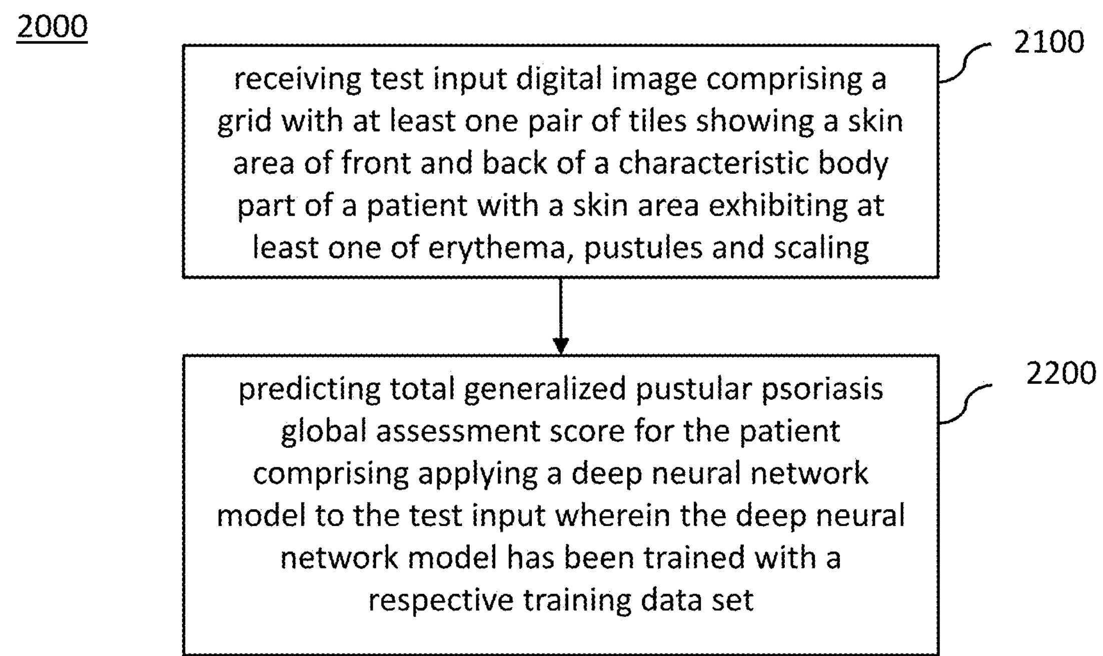
Figures 3A, 3B:
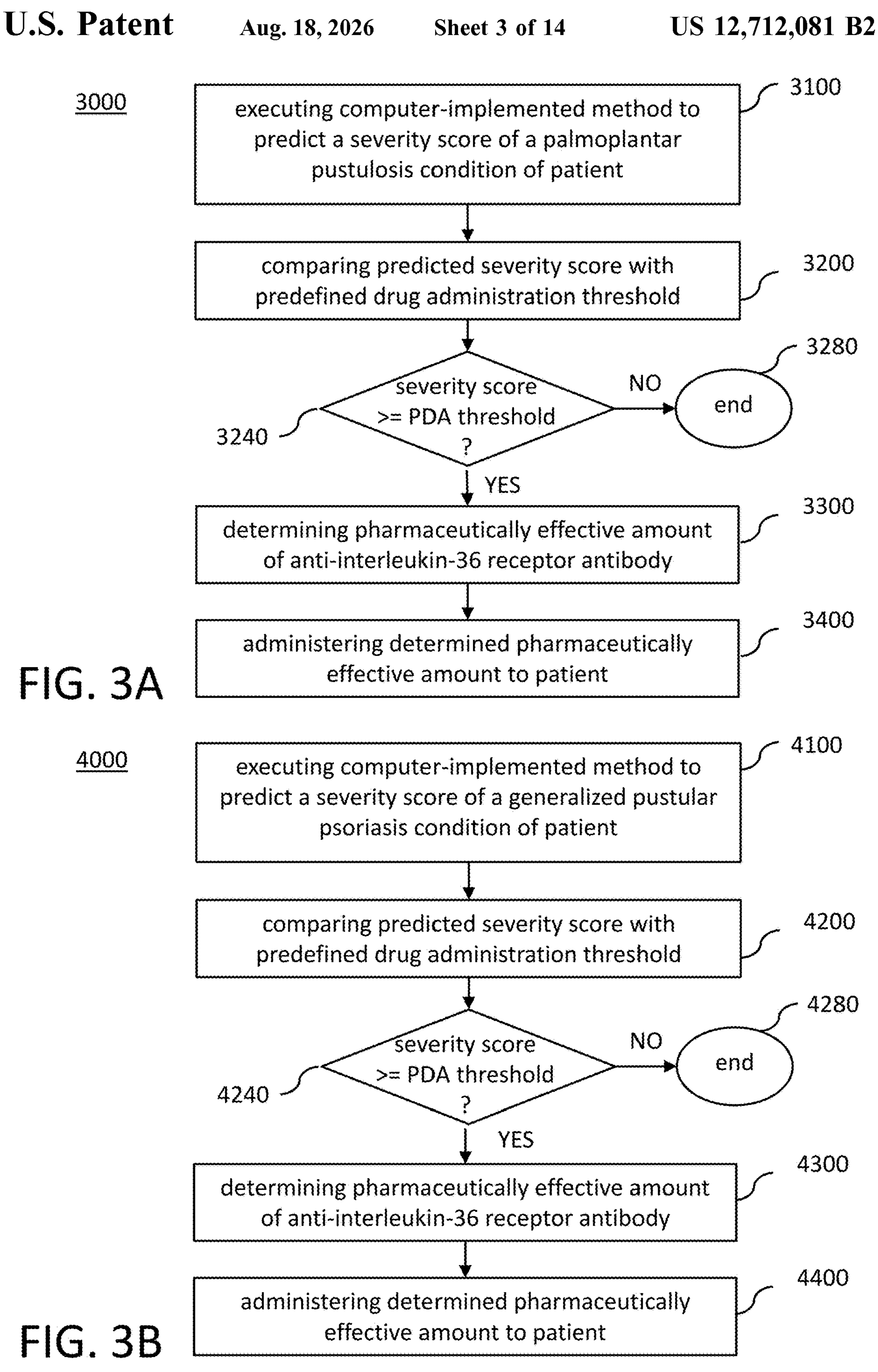
FIGS. 3A, 3B are simplified flowcharts of methods of treatment of PPP/GPP conditions of a patient in accordance with two aspects of the description.

FIG. 1 shows a simplified block diagram of a computer system 100 for predicting severity of a neutrophilic dermatosis condition of a patient 10 according to an embodiment. In the example, the system is configured to predict a patient's PPP and/or GPP condition. However, the system may be configured to also cover other types of neutrophilic dermatosis condition. FIGS. 2A and 2B are simplified flowcharts of computer-implemented methods 1000, 2000 for predicting severity of PPP/GPP conditions of the patient 10. The methods can be performed by the computer system 100. FIGS. 3A, 3B are simplified flowcharts of methods 3000, 4000 of treatment of PPP/GPP conditions of the. Methods 3000, 4000 include methods 1000, 2000 respectively. All of the steps of methods 1000, 2000 can be performed by the system 100. Also, most of the method steps of methods 3000, 4000 can be performed by system 100. In the following, the computer system 100 is described in the context of the method steps which can be executed by the system. Therefore, the following description refers to reference numbers of system figure FIG. 1 and the method FIGS. 2A, 2B, 3A, and 3B.

System 100 is communicatively coupled with an image source (e.g., a digital camera 20 or a pre-processor (from the system perspective) which can merge single images of the digital camera into grid images 21). A person skilled in the art may use standard interfaces (not shown) for exchanging digital image data for the communicative coupling. The digital camera is used for capturing images skin areas on characteristic body parts of the patient 10. Depending on the disease for which a severity level (score) is to be predicted, different characteristic body parts of the patient are relevant. For example, for the assessment of PPP severity, the characteristic body parts are left and right palm, as well as left and right sole. For the assessment of GPP severity, the characteristic body parts are trunk, left and right lower limb, left and right upper limb. The camera 20 is used to capture at least one pair of images which shows the back and front of one characteristic body part. In cases where multiple characteristic body parts show disease symptoms, it can be advantageous to record multiple pairs of images with one pair for each affected body part. For example, for PPP severity prediction, a pair of images may be captured for the left palm (back and front) and a further pair of images may be captured for the right sole (back and front) of the patient 10. The pair(s) of images are then merged into a grid image 21 which includes pairs of tiles with each pair of tiles including a back and front image of a particular characteristic body part. Advantageously, each tile is of the same size. Some cameras may include such a merge function. However, the merging can also be performed by a pre-processor providing such merging function. It is to be noted that from the perspective of the camera it is actually a post-processing step. However, from the perspective of the system 100, the raw images a pre-processed before being received as grid images.

Figures 4, 5:
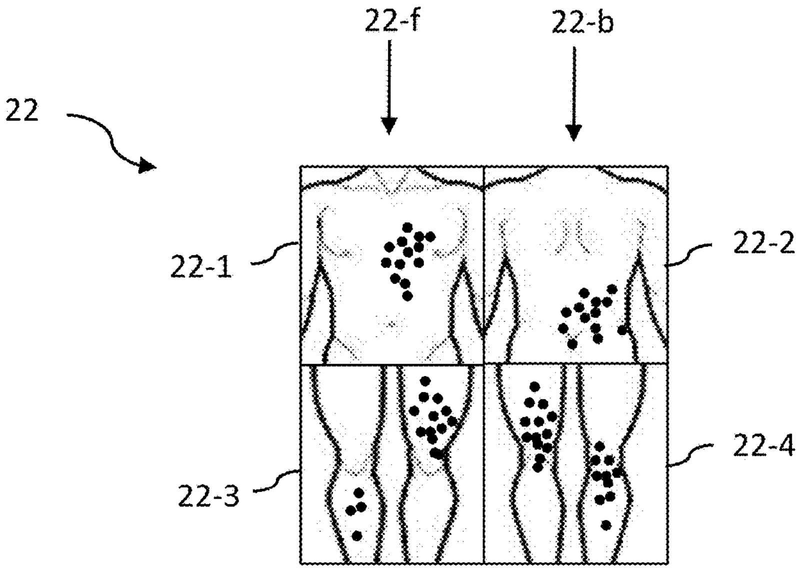
FIG. 4 is a schematic illustration of an example test input grid image.
FIG. 5 illustrates example embodiments of severity scores.
Figure 11A:
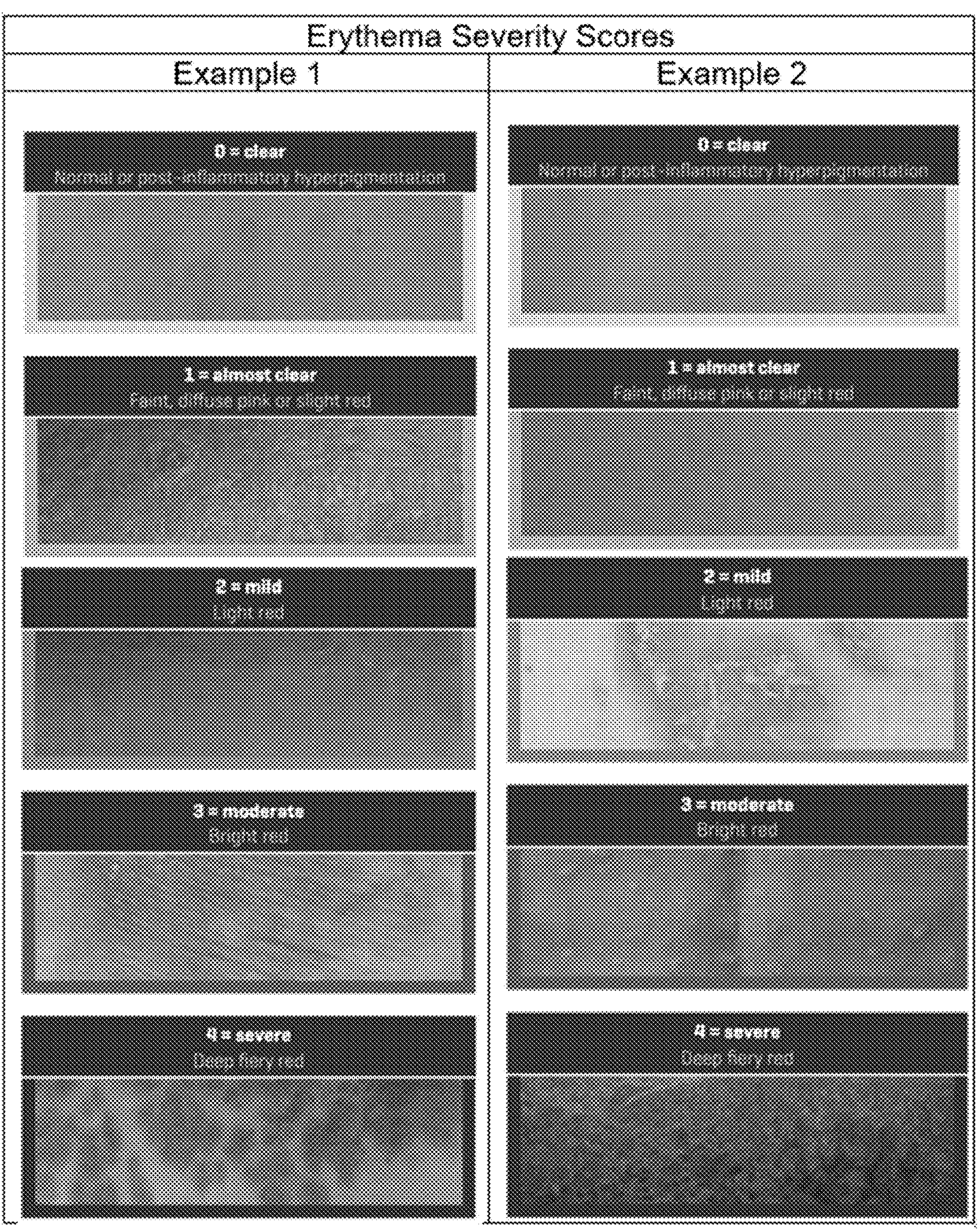
FIG. 11A shows an example of erythema severity scores (on a five-point severity scale of zero to four as shown) in digital images of skin lesions from patients with GPP.
Figure 11B:
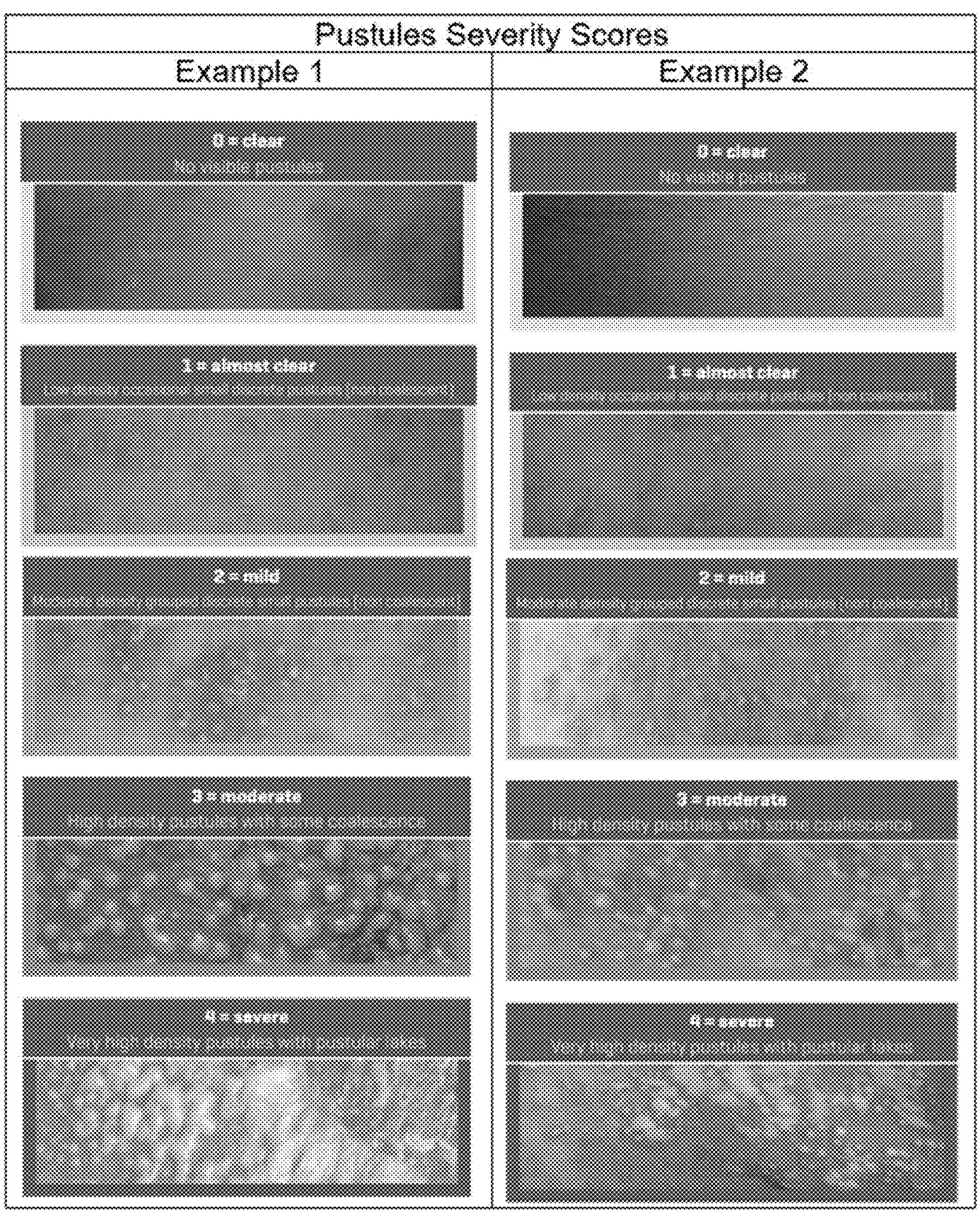
FIG. 11B shows an example of pustules severity scores (on a five-point severity scale of zero to four as shown) in digital images of skin lesions from patients with GPP.
Figure 11C:
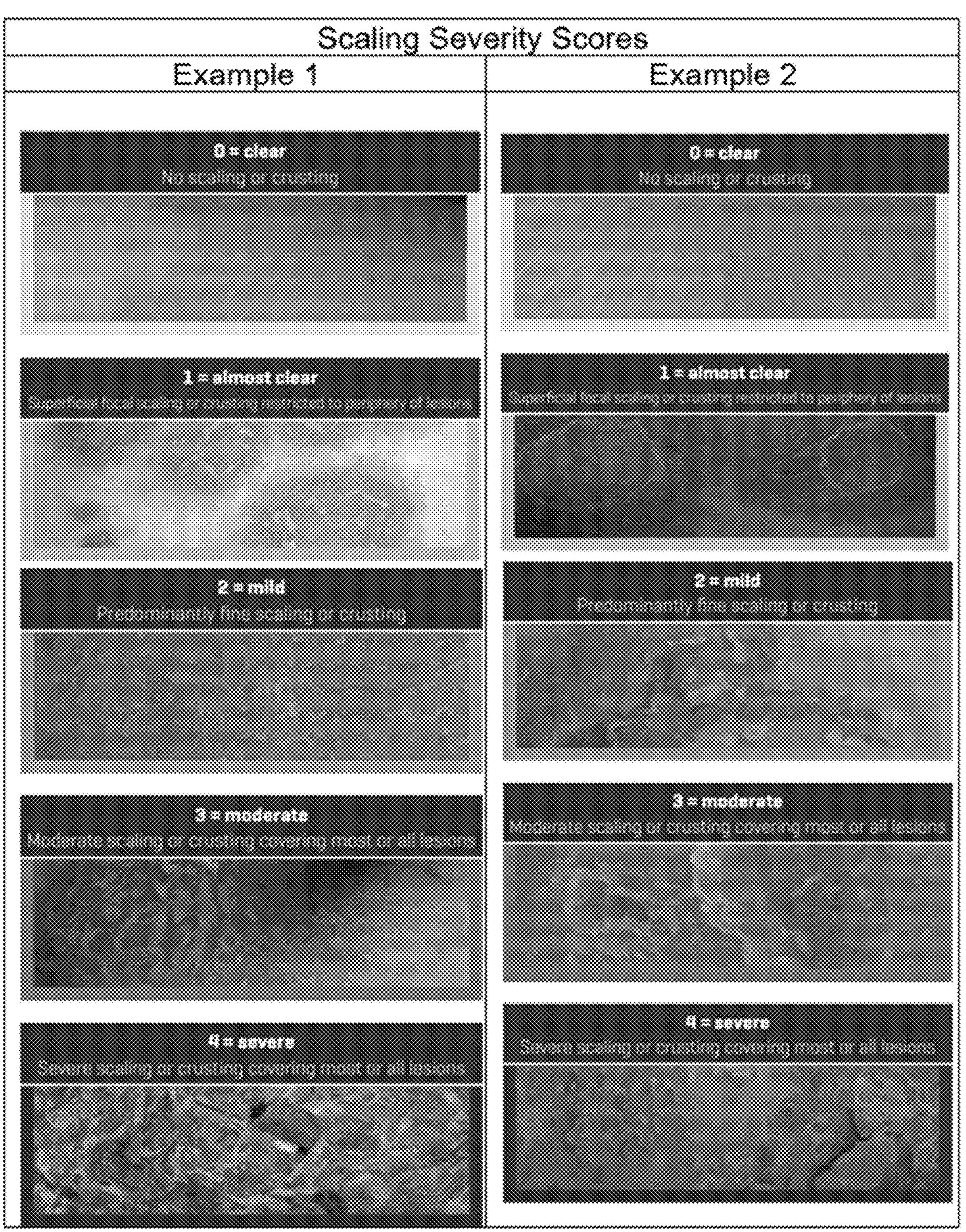
FIG. 11C shows an example of scaling severity scores (on a five-point severity scale of zero to four as shown) in digital images of skin lesions from patients with GPP.

Turning briefly to FIG. 4, a grid image 21 is illustrated which is suitable for GPP severity prediction because it includes tiles 22-1 to 22-4 showing skin areas on body parts which are characteristic body parts for GPP analysis. In the example, a first pair of tiles 22-1, 22-2 shows the front 22-*f* and the back 22-*b* of the patient's trunk. The black dots schematically illustrate skin lesions showing ND symptoms erythema, pustules or scaling. A second pair of tiles 22-3, 22-4 shows the front 22-*f* and the back 22-*b* of the patient's lower limbs (left and right). The grid image 21 could also include pairs of tiles showing back and front of the patient's upper limbs. For providing an impression of the visual appearance of ND symptoms on patient's skin lesions, FIGS. 11A to 11C show real world skin lesion images with erythema, pustules and scaling symptoms for various severity levels. FIG. 11A shows two examples for erythema symptoms with associated individual severity scores on a five-point scale (0 to 4) covering the severity levels clear, almost clear, mild, moderate and severe. Similarly, FIG. 11B illustrates two examples for pustules symptoms with respective individual severity scores. Similarly, FIG. 11C illustrates two examples for scaling symptoms with respective individual severity scores.

System 100 now receives 1100, 1200 the grid image 21 as a test input digital image which serves as input to the system's predictor module 110. The predictor 110 uses at least one respectively trained deep neural network model DNN1 to predict a total palmoplantar pustulosis global assessment score (PPPGA) (first aspect) and/or a total Generalized Pustular Psoriasis Physician Global Assessment score (PPPGA) 111 (second aspect) for the patient 10. DNN1 has been trained by a training module 190 which may be an integrated module of system 100, or it may be a module provided on a remote computer which is communicatively coupled with system 100 so that the trained DNN1 can be provided to the predictor 110. In FIG. 1, DNN1 is illustrated by its classification layers. However, the entire topology of DNN1 is more complex as explained in FIG. 6A. The training module 190 is communicatively coupled with or includes a data storage providing a training image data set 300. The training data set 300 includes a plurality of training images having the same structure as the test input 21 (i.e., the grid structure with at least two tiles). The training images have been captured from a plurality of test patients 90 selected in accordance with predefined inclusion/exclusion criteria which ensure that the training patients 90 have, respectively, a palmoplantar pustulosis history and/or generalized pustular psoriasis history without conflicting diseases. Thereby, the training data set comprises multiple training images 310 to 360 of each training patient which were captured at different time points during a predefined minimum time interval. In an experimental implementation, about 50% of the training patients did not show pustules, scaling or erythema after treatment with Spesolimab. However, the flare would come back if the treatment is being stopped for such training patients. In the test implementation, the training patients stayed in the study for at least three months. During this period, the skin presentation of each training patient was reevaluated every week (i.e., once a week but not necessarily always on the same week day). That is, in this test implementation the minimum time interval was three months.

The inclusion criteria which were used for the selection of training patients to provide training images showing ND symptoms are (i.e., patients qualified as training patients if they meet the following criteria):

- 1a. Patients with a GPPGA score of 0 or 1 and a known and documented history of GPP (per ERASPEN criteria) regardless of IL36RN mutation status, and in addition with previous evidence of fever, and/or asthenia, and/or myalgia, and/or elevated C-reactive protein, and/or leucocytosis with peripheral blood neutrophilia (above the upper limit of normal [ULN]), OR
- 1b. Patients with an acute flare of moderate-to-severe intensity meeting the ERASPEN criteria of GPP, with a known and documented history of GPP (per ERASPEN criteria) regardless of IL36RN mutation status, and in addition with previous evidence of fever, and/or asthenia, and/or myalgia, and/or elevated C-reactive protein, and/or leucocytosis with peripheral blood neutrophilia (above ULN), OR
- 1c. Patients experiencing their first episode of an acute GPP flare of moderate-to-severe intensity with evidence of fever, and/or asthenia, and/or myalgia, and/or elevated C-reactive protein, and/or leucocytosis with peripheral blood neutrophilia (above ULN). For these patients, the diagnosis will be confirmed retrospectively by a central external expert/committee.
- 2. Patients may or may not be receiving background treatment with retinoids and/or methotrexate and/or cyclosporine. Patients must discontinue retinoids/methotrexate/cyclosporine prior to receiving the first dose of spesolimab or placebo.
- 3. Male or female patients, aged 18-75 years at screening.
- 4. Signed and dated written informed consent prior to admission to the study in accordance with ICHGCP and local legislation prior to start of any screening procedures.
- 5. Women of childbearing potential must be ready and able to use highly effective methods of birth control per ICH M3 (R2) that result in a low failure rate of less than 1% per year when used consistently and correctly. A woman is considered of childbearing potential (WOCBP), i.e. fertile, following menarche and until becoming postmenopausal unless permanently sterile. Permanent sterilisation methods include hysterectomy, bilateral salpingectomy and bilateral oophorectomy. Tubal ligation is not a method of permanent sterilisation. A postmenopausal state is defined as no menses for 12 months without an alternative medical cause.

The exclusion criteria which were used for the selection of training patients are (i.e., patients were not selected as training patients if any of the following criteria apply):

1. Patients with synovitis-acne-pustulosis-hyperostosis-osteitis syndrome.
2. Patients with primary erythrodermic psoriasis vulgaris.
3. Patients with primary plaque psoriasis vulgaris without presence of pustules or with pustules that are restricted to psoriatic plaques.
4. Drug-triggered acute generalized exanthematous pustulosis.
5. Immediate life-threatening flare of GPP or requiring intensive care treatment, according to the investigator's judgement. Life-threatening complications mainly include, but are not limited to cardiovascular/cytokine-driven shock, pulmonary distress syndrome or renal failure.
6. Severe, progressive or uncontrolled hepatic disease, defined as >3-fold ULN elevation in aspartate transaminase or alanine transaminase or alkaline phosphatase, or >2-fold ULN elevation in total bilirubin.
7. Treatment with:
   - a. Any restricted medication as specified in Supplementary Table 1, or any drug considered likely to interfere with the safe conduct of the study, as assessed by the investigator;
   - b. Any prior exposure to spesolimab or another IL36R inhibitor.
8. Patients with dose escalation of their maintenance therapy with cyclosporine and/or methotrexate and/or retinoids within the 2 weeks prior to receiving the first dose of spesolimab/placebo.
9. The initiation of systemic agents such as cyclosporine and/or retinoids and/or methotrexate 2 weeks prior to receiving the first dose of spesolimab/placebo.
10. Patients with congestive heart disease, as assessed by the investigator.

11. Active systemic infections (fungal and bacterial disease) during the last 2 weeks prior to receiving first drug administration, as assessed by the investigator.
12. Increased risk of infectious complications (e.g. recent pyogenic infection, any congenital or acquired immunodeficiency [e.g. human immunodeficiency virus (HIV)], past organ or stem cell transplantation), as assessed by the investigator.
13. Relevant chronic or acute infections including HIV or viral hepatitis. For patients screened while having a flare (inclusion criteria 1b or 1c), if Visit 1 HIV or viral hepatitis results are not available in time for randomisation, these patients may receive randomised treatment as long as the investigator has ruled out active disease based on available documented history (i.e. negative HIV and viral hepatitis test results) within 3 months prior to Visit 2. A patient can be re-screened if the patient was treated and is cured from acute infection.
14. Active or latent tuberculosis (TB): QuantiFERON® (or if applicable, T-Spot®) TB test will be performed at screening. If the result is positive, the patient may participate in the study if further work up (according to local practice/guidelines) establishes conclusively that the patient has no evidence of active tuberculosis. Patients with active TB must be excluded. If presence of latent tuberculosis is established, then treatment should have been initiated and maintained according to local country guidelines. For patients screened while having a flare (inclusion criteria 1b or 1c), if the TB test results are not available in time for randomisation, these patients may receive randomised treatment (provided they meet all other inclusion/exclusion criteria) as long as the investigator has ruled out active disease based on available documented history (i.e. negative for active TB) within 3 months prior to Visit 2.
15. History of allergy/hypersensitivity to a systemically administered trial medication agent or its excipients.
16. Any documented active or suspected malignancy or history of malignancy within 5 years prior to screening, except appropriately treated basal or squamous cell carcinoma of the skin or in situ carcinoma of uterine cervix.
17. Currently enrolled in another investigational device or drug study, or less than 30 days since ending another investigational device or drug study(s) or receiving other investigational treatment(s).
18. Women who are pregnant, nursing or who plan to become pregnant while in the trial. Women who stop nursing before the study drug administration do not need to be excluded from participating; they should refrain from breastfeeding up to 16 weeks after the study drug administration.
19. Major surgery (major according to the investigator's assessment) performed within 12 weeks prior to receiving the first dose of study drug or planned during the study, e.g. hip replacement, aneurysm removal, stomach ligation, as assessed by the investigator.
20. Evidence of a current or previous disease, medical condition (including chronic alcohol or drug abuse or any condition) other than GPP, surgical procedure, psychiatric or social problems, medical examination finding (including vital signs and electrocardiogram) or laboratory value at the screening outside the reference range that in the opinion of the investigator is clinically significant and would make the study participant unreliable to adhere to the protocol, comply with all study visits/procedures or to complete the trial, compromise the safety of the patient or compromise the quality of the data.

Each training image is annotated with one or more severity scores associated with erythema, pustules and scaling as the ground truth reflecting-dependent on the to-be-assessed ND condition—the severity of the palmoplantar pustulosis condition and/or the generalized pustular psoriasis condition of the respective training patient at the time-point the training image was captured. For example, Generalized Pustular Psoriasis Physician Global Assessment (GPPGA) relies on the clinical assessment of the patient's skin presentation. It is a modified PGA, a physician's assessment of psoriatic lesions, which has been adapted to the evaluation of patients with generalized pustular psoriasis (GPP). An investigator (or qualified site personnel) may score the erythema, pustules and scaling of all psoriatic lesions on a training image from 0 to 4. In one implementation, each component is graded separately and the training image is annotated respectively with three individual ground truth values. In this implementation, for each symptom (erythema, pustules and scaling) an individual deep neural network may be trained. In another implementation, an average is determined from the individual scores as a composite score and the training image is annotated with the composite score as the ground truth. For example, a composite mean score may be computed as the sum of the individual scores for erythema, pustules and scaling divided by 3. For example, a total GPPGA score is "0" if the mean="0" for all three components, "1" if the mean is in the range "0" to <"1.5", "2" if the mean is in the range "1.5" to <"2.5", "3" if the mean is in the range "2.5" to <"3.5", and "4" if the mean is ≥"3.5". A lower score indicates a lesser severity, with, for example, 0 being clear and 1 being almost clear. To receive a score of 0 or 1, the patient should be afebrile in addition to the skin presentation requirements. The following table 1 illustrates a scoring example for GPPGA when using a five-point severity scale.

TABLE 1 five-point severity scale example for GPPGA

| Score | Erythema | Pustules | Scaling |
|---|---|---|---|
| 0 (clear) | Normal or postinflammatory hyperpigmentation | No visible pustules | No scaling or crusting |
| 1 (almost clear) | Faint, diffuse pink or slight red | Low-density occasional small discrete pustules (noncoalescent) | Superficial focal scaling or crusting restricted to periphery of lesions |
| 2 (mild) | Light red | Moderate density grouped discrete small pustules (noncoalescent) | Predominantly fine scaling or crusting |
| 3 (moderate) | Bright red | High-density pustules with some coalescence | Moderate scaling or crusting covering most or all lesions |
| 4 (severe) | Deep fiery red | Very high-density pustules with pustular lakes | Severe scaling or crusting covering most or all lesions |

FIG. 5 illustrates the above five-point scale example 112*a* used as ground truth values for training the deep neural network model(s). In this implementation, of course the predicted severity score classification for a given test input image is also one of the score values on the five-point scale 112*a*. In an alternative implementation, the system was trained using only a three-point scale 112*b* where "almost clear" and "mild" are represented by a common score value "1" and "moderate" and "severe" are represented by a common score value "3". Appropriate prediction/classification accuracy could also be reached with this implementation.

Figure 6A:
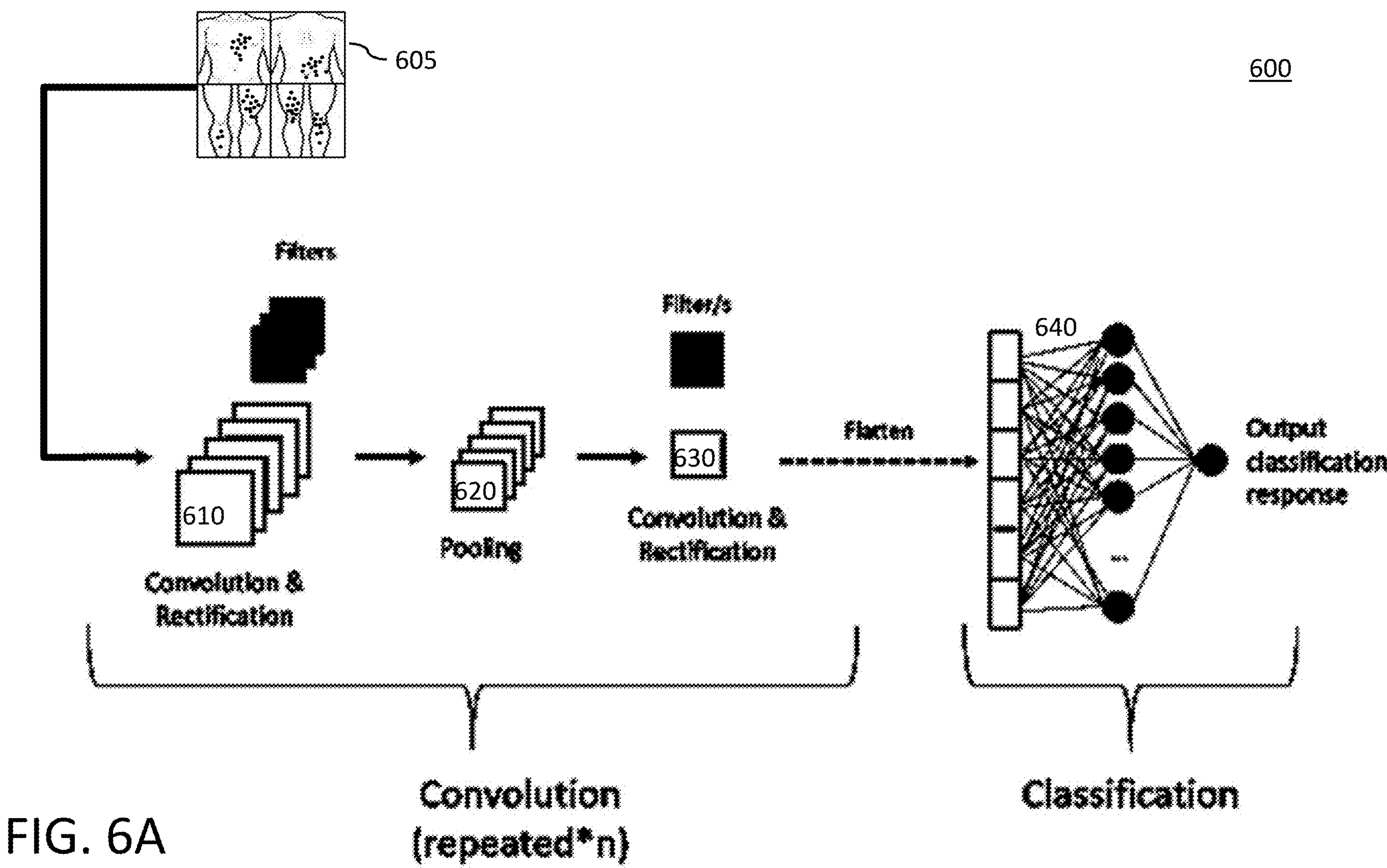
FIG. 6A shows details of the deep neural network model used by the predictor module according to an embodiment.

In one embodiment (the first aspect), the predictor module 110 predicts 1200, 2200 a total palmoplantar pustulosis global assessment score for the patient 10. In another embodiment (the second aspect), the predictor module 110 predicts a total Generalized Pustular Psoriasis Physician Global Assessment score 111. For this purpose, the predictor 110 applies the one or more respectively trained deep neural network models DNN1 to the received test input 21. As explained earlier, the only difference between the first and second aspects is in the characteristic body parts for the respective ND condition which are shown on the training images. FIG. 6A illustrates an example topology 600 for a deep neural network model used by the predictor 110.

Turning now to FIG. 6A, the figure depicts an example topology 600 of the deep neural network model (DNN1 in FIG. 1) where the model has been trained by respective training data to predict an outcome based on an input image. In the figure, an input image 605 is shown with four tiles illustrating ND symptoms on characteristic body parts of the patient to be assessed. For the training of the neural network, skin images of patients with and without generalized pustular psoriasis (GPP) were used as training images. The training data includes different types of symptoms like scaling, and/or pustulation, and/or erythema, with varying severities. For example, in case of GPP, the neural network model learns whether a person has GPP, if erythema and/or pustules and/or scaling is present, the stage/degree/scaling score of the erythema and/or pustules and/or scaling if they are present, and outputs individual scores for symptoms, as well as total Generalized Pustular Psoriasis Physician Global Assessment (GPPGA) score and Generalized Pustular Psoriasis Area and Severity Index (GPPASI). Similarly, a person skilled in the art can train the deep neural network to identify the presence of PPP without further explanation.

The topology 600 includes a convolutional neural network (CNN). The first stage of a CNN is feature extraction, which includes convolution & rectified linear activation layers 610, 630 and pooling 620. In this stage, the model identifies key features of erythema, scaling, and pustulation and key features that determine the scores of these symptoms, and further creates feature detectors to identify if these features are present in new input images. The second stage of the CNN is classification which incorporates an artificial neural network 640 (fully connected layers of DNN1) using the output/identification from the convolution stage and classifies it as containing erythema+score and/or containing pustulation+score and/or containing scaling+score, or asymptomatic, or with a single severity score expressing a composite mean value for the presence of all three symptoms.

Figure 7A:
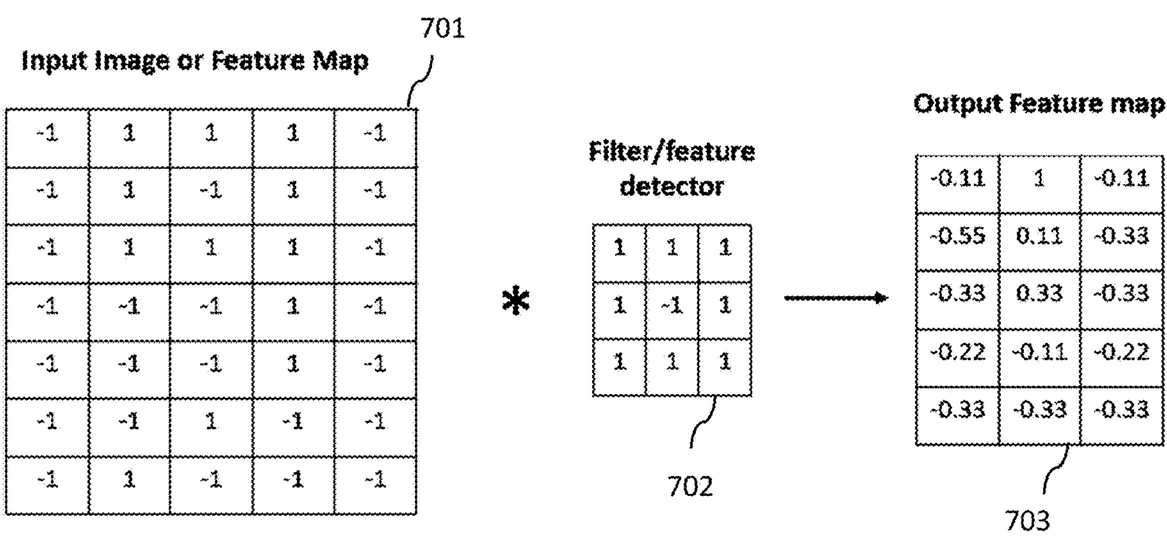
FIG. 7A depicts an example convolution step of a CNN.

FIG. 7A depicts an example of the convolution step in a CNN. This step utilizes the input data 701 to create feature maps 703, or feature detection tools. For example, when using back propagation, the model learns features, and creates feature detectors, which can detect these features in new images for proper classification. A "filter" is another term used for feature detection tool, and these two terms are used interchangeably. FIG. 7A is an example of how an image is scanned by a specific feature detector 702. FIG. 7A depicts a 7×5 pixel input image 701 scanned using a 3×3 filter window 702 with stride of 1. In each window, the individual numbers representing the pixels of the image are multiplied by the number in the corresponding location in the 3×3 feature detector. The average of the products is computed and imputed into a new feature map 703. The filter moves across the image in strides of 1 and repeats the same process in each window until the image is fully scanned by the filter and a complete feature map is created.

Figure 7B:
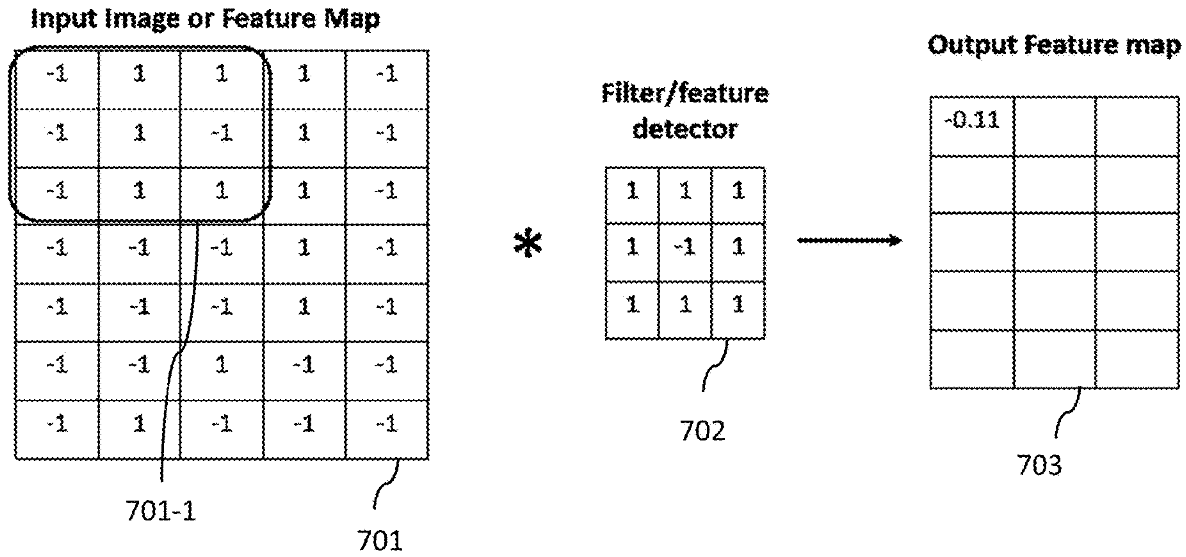
FIG. 7B depicts an example computation of a filter being applied to a window on an input image to create a feature map, or to create a new feature map from an input feature map.

FIG. 7B depicts the computation of the first scanning window 701-1 multiplied by the filter 702, which sums and averages to −0.11, which is imputed as the first value in the feature map 703. The output feature map 703 represents whether the specific feature was detected or not. The calculations are representative calculations, and values −1 and 1 were used for simplicity, but the values represent the pixels, which have a much larger range. The input image in FIGS. 7A, 7B is either an input image or a feature map as explained below.

The scanning window size, filter, and stride number are all variables and hyperparameters that are tuned to train the model. The actual values in the filters are learned by the model using back propagation and cannot be specified. Filters represent features, and when an image is filtered by a filter, it is being scanned for that particular feature. Through training, the network determines which features are important and creates filters for each feature. FIGS. 7A, 7B depict the convolution operation for one filter, but the operation is performed to produce any number of filters.

Figure 8:
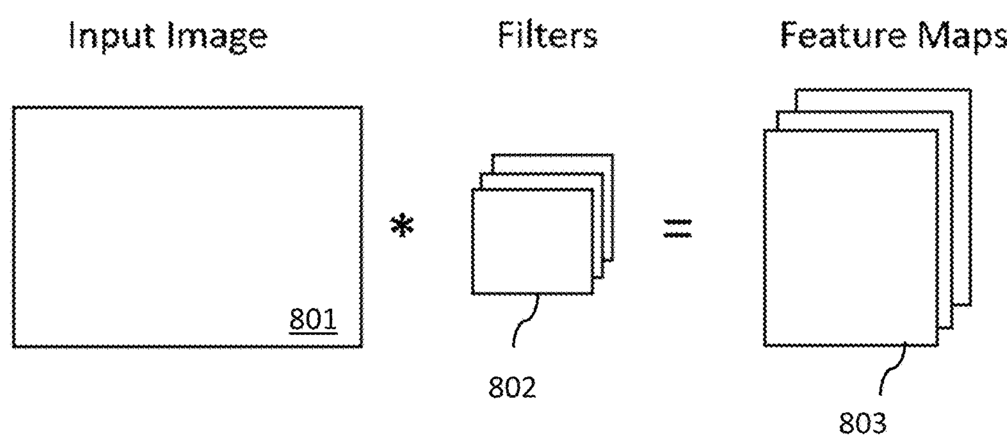
FIG. 8 depicts an example of three filters being applied to an input, producing three new feature maps.
Figure 9:
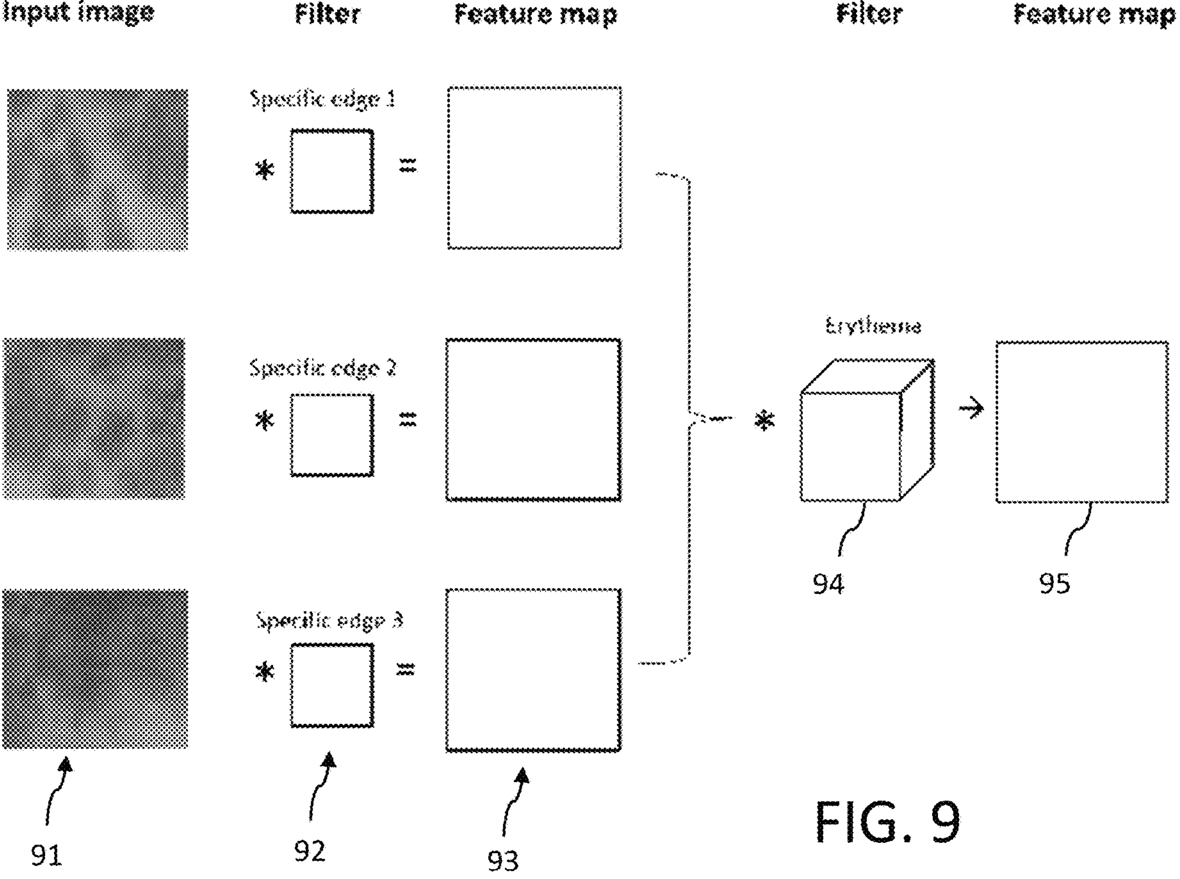
FIG. 9 depicts an example embodiment of subsequent convolutions in a CNN for erythema.

FIG. 8 embodies an example of multiple filters 802 being applied to an input image 801 producing multiple feature maps 803. More filters are subsequently applied to the output feature maps, and combined feature maps. In general, in a CNN, lower layers detect simple structures (e.g., different types of edges), While going deeper (i.e., towards layers closer to the output of the CNN), the layers build on top of each other and learn to encode more complex patterns. Taking this complex patterns together the model can detect eventually patters which correspond to erythema or other symptoms. FIG. 9 depicts a simplified block diagram of a subsequent filter 94 being applied to the combination of feature maps 93 that have already been filtered (by filters 92). As shown in FIG. 9, the first layer of filters 92 applied to the image 91 detects different types of edges in an image that are indicative or erythema, and the second filter is applied to the combination of the output feature maps, which is indicative of erythema. FIG. 9 simplifies the process of detecting erythema, while in reality, there are many more layers of filters before diagnosing erythema. The earlier filters are more similar to edges, shapes, and traits of erythema and more subsequent layers are less subtle in representing erythema. Filters following the erythema diagnostic detect more features that characterize the score of erythema. The model also includes the convolution process with filters that ultimately diagnose scaling and pustules and their state/scaled scores, as well as a global score of GPP (or PPP according to the first aspect).

A rectifier function, or rectified linear activation unit (ReLU), is applied to the output feature maps from each filter to increase nonlinearity in the model. ReLU essentially replaces all negative values in feature maps with the value "0", and maintains all values with a positive number. An example of a feature map 703 being rectified is depicted in FIG. 10. The feature map 703 initially contains positive and negative values, and after applying the rectifier function, the negative values are replaced with 0 in the rectified feature map 704. Images naturally contain nonlinear features like transitions between pixels, and borders, but the convolution operation might impose linearity. The rectifier serves to break up the linearity and helps maintain the model nonlinearity.

Figures 10A, 10B:
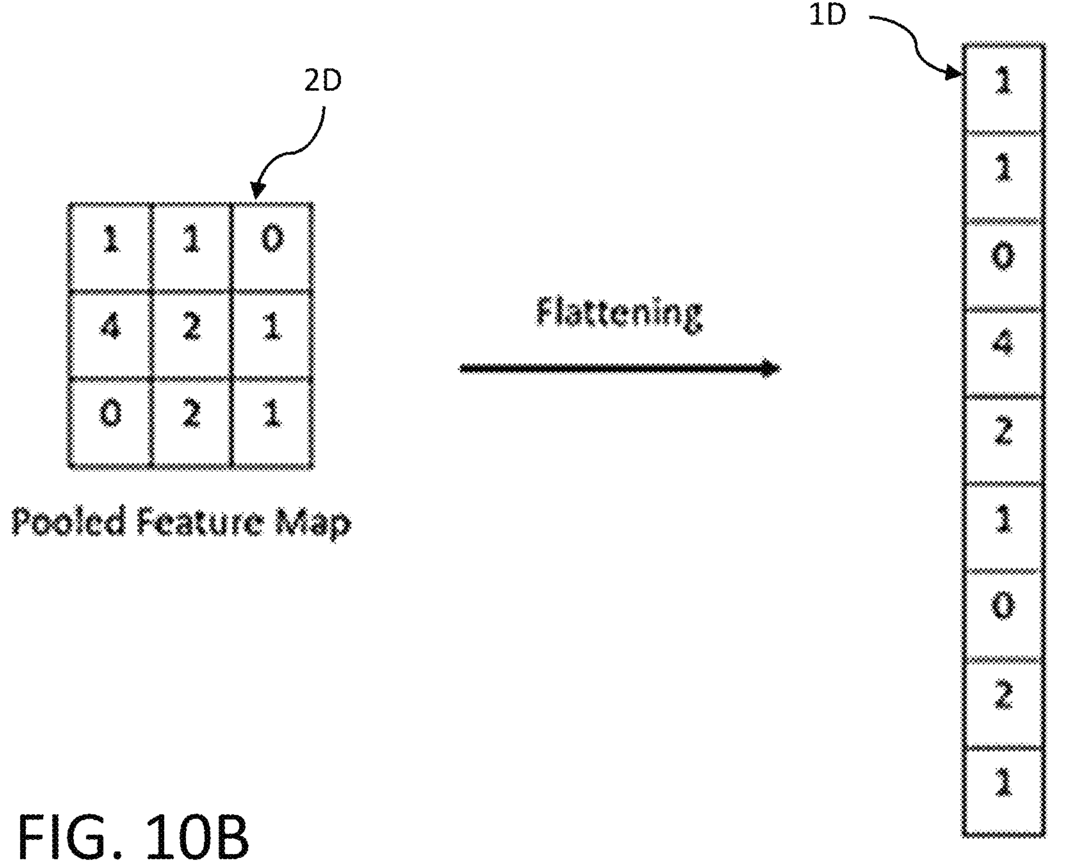
FIG. 10A depicts an example of a feature map being transformed by a rectifier function.
FIG. 10B depicts an example of flattening a pooled feature map from a 2D array to a 1D array.
Figure 10C:
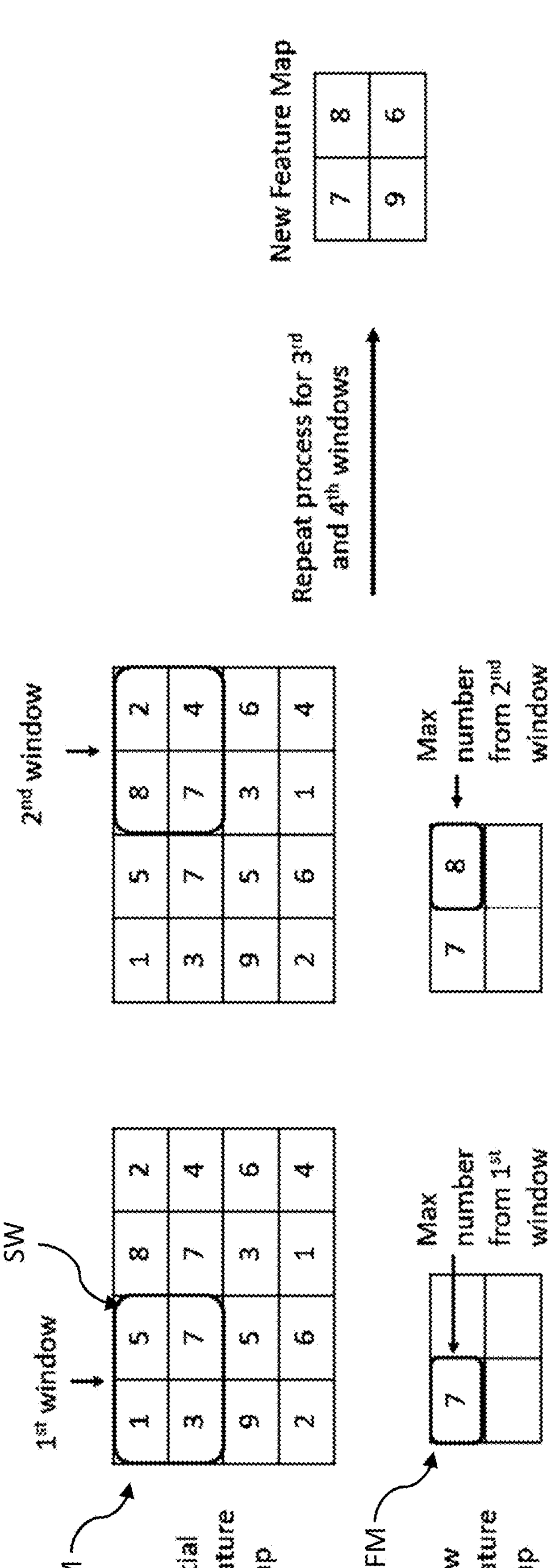
FIG. 10C depicts an example of Max Pooling.

Output from the rectifier is pooled to reduce size/dimensions of the feature map. FIG. 10C is an example of reducing a 4×4 feature map IFM to a 2×2 feature map NFM by "max pooling". In this example, the initial feature map is scanned using a 2×2 window SW with a stride of 2, and the maximum number from each window is converted to the new feature map. Other types of pooling include mean pooling, where the average from the window is imputed into the new feature map, and sum pooling, where the sum of the numbers in the window is imputed into the new feature map. All pooling techniques effectively reduces the dimensions of the feature map.

The feature map data is flattened out from 2D arrays to 1D arrays so that it can later be inserted into an artificial neural network for classification. FIG. 10B is an example of fattening out a 3×3 2D array into a 1D array. The 1D array finally runs through an artificial neural network (ANN) for classification (cf. artificial neural network 640 in FIG. 6A). The convolution handles the feature extraction portion of the network, and the ANN at the latter end of the model handles the variety in the input so that it can classify the variety correctly. The convolution detects the features, and the ANN processes variety in the location of those features. To further account for variety, data augmentation may be applied to the initial input images of people's skin to generate more samples with more variety. Augmenting data includes rotating images and changing the scale of images, which helps train the model for variety.

In one implementation, an internal dataset of images from patients with GPP was augmented and used to train a deep neural network model. Data was augmented which includes rotating, enlarging, and reducing the images to generate variations in input data and create more samples. In this implementation, an existing pre-trained model was used for transfer learning and trained with the GPP images. Possible embodiments of pre-trained deep neural network models include but are not limited to:

Convolutional Neural Networks (CNNs), such as ResNet, EfficientNet and ConvNext architectures, Vision Transformers (ViTs), and combination network, which stacks convolutional layers and attention layers.

In an embodiment of the deep neural network, the output is classified as a score for GPP. Another embodiment includes a classification for GPP with a score, a classification for normal skin and/or a classification for a skin lesion that is not GPP and also not normal. This embodiment flags images as containing a skin area that is not normal and potentially at risk of other infections and should be further analyzed.

During the convolution stage of the deep neural network, a model according to the second aspect determines which features represent GPP, and embodiments of this layer include but are not limited to: edges, colors, and shapes representative of GPP, as well as pustule counting. These features are identified and are used to train the model during training. These features are also determined during training using the above-mentioned alternative algorithms including but not limited to Convolutional Neural Networks (CNNs), like the ResNet (residual neural network), EfficientNet and ConvNext architectures, Vision Transformers (ViTs) and combination network, which stacks convolutional layers and attention layers. In some implementations, the image processing may also include background removal, skin lesion localization via handcrafted features, including the color, texture, border irregularity, and asymmetry and a learned classifiers for example U-Net architecture for semantic segmentation.

Turning back to FIG. 1, in one embodiment, the above-described classification of ND conditions using the deep neural network DNN1 trained with the training image data set 300 may be enhanced by using, in addition, clinical tabular data 200 for the training of the classifier. When using the predictor 110 in this embodiment to assess the test input of patient 10, in addition to the image grid 21, the patient's test input further comprises clinical tabular data 30 of the patient. Thereby, a particular feature set 30 of clinical tabular data and a respective digital image 21 are associated with the same severity of the patient's condition. This is typically achieved by capturing such data on the same day. Of course, the same is true for the training data used for training the classifier. In the example, each training image 310 to 360 has such an associated clinical tabular training data set 210 to 260, respectively.

Figure 6B:
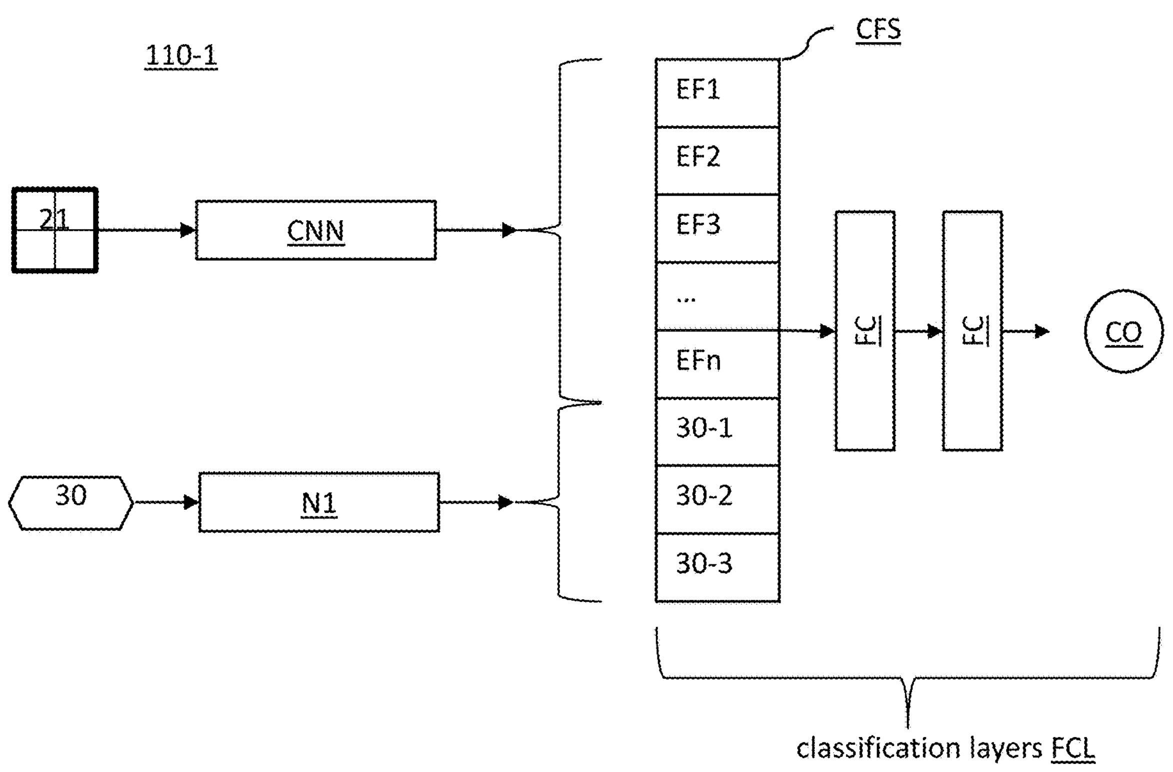
FIGS. 6B, 6C illustrate alternative implementations of the predictor module including clinical tabular data as further test input.
Figure 6C:
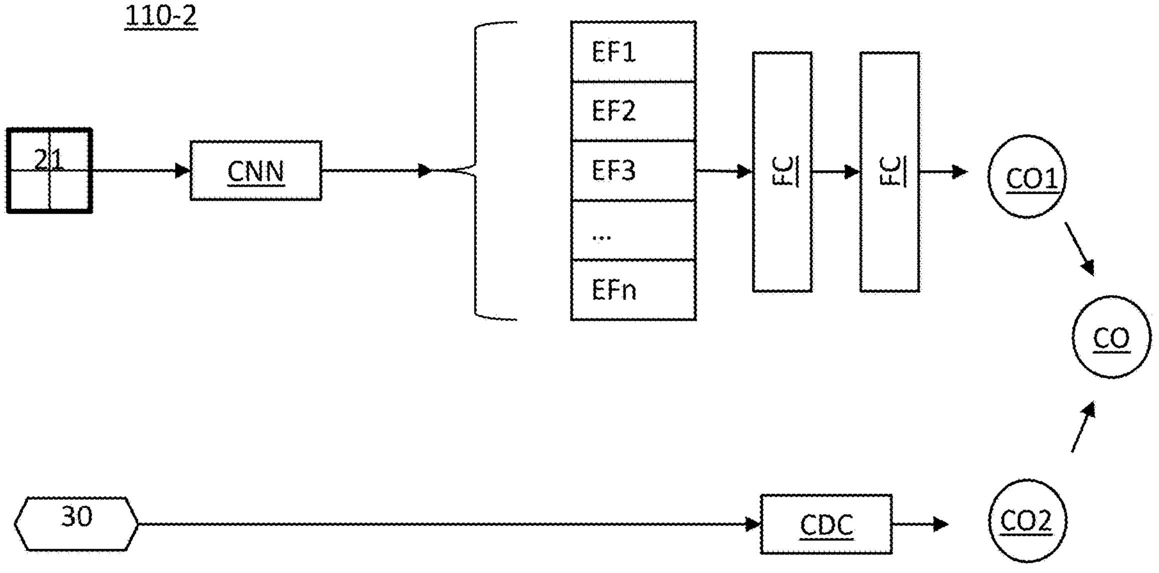

FIGS. 6B and 6C illustrate two alternative implementations 110-1, 110-2 of the "clinical tabular data" embodiment. In FIG. 6B, the predictor 110-1 is configured to combine feature set 30 of clinical tabular data 30-1, 30-2, 30-3 of the patient with features EF1 to EFn extracted from respective digital image 21 of the patient by the CNN for the severity assessment of said patient. That is, the input layer CFS of the classification neural network is extended in comparison to FIG. 6A with the clinical tabular data features 30-1, 30-2, 30-3. Advantageously, the clinical tabular data features 30-1, 30-2, 30-3 are normalized by normalizer N1 before being concatenated to the respective features EF1 to EFn extracted from the convolutional layers CNN of the deep neural network. The concatenated feature vector CFS is then processed by fully connected layers FC representing the classification layers FCL of the deep neural network. The classification output CO is then provided by the last classification layer. In this implementation, the training module uses respective enhanced training data comprising the plurality of training images 310 to 360 and associated feature sets 210 to 260 of clinical tabular data features to train the deep neural network DNN1 (cf. FIG. 1).

Examples of clinical tabular data for increasing a patient's feature set may include, but are not limited to: Fever, C-reactive protein (CRP), White Blood Cells (WBC), and Albumin.

Combining such clinical tabular data features with those features extracted from the respective digital images, the classifier achieves a higher prediction accuracy compared with just using the images alone.

FIG. 6C illustrates an alternative implementation 110-2 for the clinical tabular data embodiment. The predictor 110-2 includes an image path (upper part of FIG. 6C) basically implementing the deep neural network as described with FIG. 6A. The CNN is used to extract features EF1 to EFn from the received grid image 21. The fully connected classification layers FC provide a first classification output CO1 (the severity level determined by the trained deep neural network). In this implementation, the predictor 110-2 further comprises a clinical data classifier CDC that has been trained on clinical tabular data features associated with the respective training images of the deep neural network model using the same ground truth. That is, if the ground truth for a training image specifies a particular severity score, the ground truth for the associated clinical tabular data set is also set to this particular severity score. The training module in this implementation uses Ensemble Learning for the clinical data classifier CDC and the deep neural network of the image path. The predictor finally combines the first output CO1 of the deep neural network model and the second output CO2 of the clinical data classifier CDC into a single severity score CO. The CDC does not use a neural network but is based on a different classifier, such as for example, Logistic regression, Gradient Boosting, Random Forest, Support Vector Machine, or other appropriate classifiers.

The methods and systems disclosed above are dedicated to the assessment of GPP and/or PPP severity of a patient's ND condition. However, a person skilled in the art will understand that the herein disclosed approach for the assessment of a patient's ND condition can also be applied to other types of neutrophilic dermatosis when using appropriate training data for training the underlying deep neural network model. For example, such other types of neutrophilic dermatosis comprise: hidradenitis suppurativa (HS); acute generalized exanthematous pustulosis; acute febrile neutrophilic dermatosis (Sweet syndrome); amicrobial pustulosis of the folds (APF); Behcet disease; Bowel bypass syndrome (bowel-associated dermatitis-arthritis syndrome); bowel-associated dermatosis-arthritis syndrome (BADAS); CARD14-mediated pustular psoriasis (CAMPS); cryopyrin associated periodic syndromes (CAPS); deficiency of interleukin-36 receptor antagonist (DIRTA); deficiency of interleukin-I receptor antagonist (DIRA); erythema elevatum diutinum; Histiocytoid neutrophilic dermatitis; infantile acropustulosis; neutrophilic dermatosis of the dorsal hands; neutrophilic eccrine hidradenitis; neutrophilic urticarial dermatosis; palisading neutrophilic granulomatous dermatitis; plaque psoriasis; pyoderma gangrenosum, acne, and hidradenitis suppurativa (PASH) syndrome; pyoderma gangrenosum (PG); pyoderma gangrenosum and acne (PAPA); pyogenic arthritis; skin lesions of Behcet's disease; Still's disease; subcorneal pustulosis (Sneddon-Wilkinson); synovitis, acne, pustulosis-hyperostosis and ostcitis (SAPHO) syndrome; rheumatoid neutrophilic dermatitis (RND), and ichthyosis (and its subtypes including Netherton syndrome or NS).

Turning back to FIG. 1, optional embodiments are now described which allow to use the herein disclosed system and methods for assessing severity of neutrophilic dermatosis with visible skin manifestation in the context of providing suitable treatment to a patient suffering from ND. In these optional embodiments, the system further can include a severity checker module 120, and further can include an antibody dosage module 130. The corresponding methods 3000, 4000 are depicted in FIGS. 3A, 3B, wherein method 3000 is represented by a simplified flowchart for treating a patient suffering from palmoplantar pustulosis, and method 4000 is represented by a simplified flowchart for treating a patient suffering from generalized pustular psoriasis. The two methods 3000 and 4000 only differ in the first step. In method 3000, the first step 3100 is executing the computer-implemented method 1000 according to the first aspect to predict a severity score of a palmoplantar pustulosis condition of the patient. In method 4000, the first step 4100 is executing the computer-implemented method 2000 according to the second aspect to predict a severity score of a generalized pustular psoriasis condition of the patient. The remaining steps 3200 to 3400 of method 3000 correspond to the steps 4200 to 4400 of method 4000 (cf. FIG. 3B). Therefore, the details of the methods are described now for method 4000 (GPP) but equally apply to method 3000 (PPP).

After execution 4100 of the computer-implemented method 2000 the system 100 has determined a severity score 111 of a generalized pustular psoriasis condition of the patient 10. The severity checker module 120 can compare 4200 the predicted severity score 111 with a predefined drug administering threshold 2. Thereby, the predicted severity score has one of at least three severity score values 1, 2, 3 covering the severity range from clear to severe (cf. FIG. 5). It is to be noted that the reference numbers 1, 2, 3 do not represent the amount of the respective values but simply refer to the position of the respective value in severity range. In the example, the severity checker defines the second severity score value 2 (dotted background) as predefined drug administering threshold. In accordance with range 112*b* of FIG. 5, the amount of this value may correspond to the middle value "1". When using a five-point scale as in range 112*a*, the threshold value may be set to "3" for moderate. In other words, when the predictor has determined a GPP severity score for the patient, the severity checker checks 4240 if the determined (predicted) severity score is equal to or greater than the predefined drug administering threshold 2. If not (NO), the process ends 4280 because there is no need for treatment in view of the patient's current GPP condition. If YES, the severity checker can assign the patient 10 as a candidate for treatment with an anti-interleukin-36 receptor antibody.

For a patient being a candidate for treatment, system 100 can use the antibody dosage module 130 to determine 4300 a recommended dosage based on the pharmaceutically effective amount of an anti-interleukin-36 receptor antibody. The pharmaceutically effective amount has been determined in clinical studies. The based on the severity score for the patient and the drug administering threshold, the computer can now determine whether the patient should be treated with the respective dosage (e.g., an additional dosage) and make a respective recommendation. If the severity score is equal to or greater than the predefined drug administering threshold the recommended dosage can be provided to a respective drug administering entity 400 to administer 4400 to the patient the recommended dosage of the anti-interleukin-36 receptor antibody for treatment of the generalized pustular psoriasis. The antibody dosage module may allow user interaction with a medical practitioner. The recommended dosage may first be communicated to the medical practitioner for approval and the dosage recommendation or a corrected dosage may be provided to the drug administering entity 400 only upon approval by the medical practitioner.

With regard to the method 3000 for treating a patient suffering from palmoplantar pustulosis, the determined severity score may be the total palmoplantar pustulosis Global Assessment (PPPGA) score or a palmoplantar pustulosis Global Pustules (PPPGP) score. When using the five-point scale implementation, the following severity scoring may be applied: 0 if the total PPPGA score or the PPPGP score equals zero, 1 if the total PPPGA score or the PPPGP score is greater than zero but less than 1.5, 2 if the total PPPGA score or the PPPGP score is equal to or greater than 1.5 but less than 2.5, 3 if the total PPPGA score or the PPPGP score is equal to or greater than 2.5 but less than 3.5, and 4 if the total PPPGA score or the PPPGP score is equal to or greater than 3.5. If the patient exhibits a score of ≥2 for the total PPPGA score or the PPPGP score a recommended dosage based on the pharmaceutically effective amount of an anti-IL-36R antibody can be administered to the patient for PPP treatment.

An antibody according to an embodiment can be incorporated into pharmaceutical compositions suitable for administration to a patient. The compounds of the description may be administered alone or in combination with a pharmaceutically acceptable carrier, diluent, and/or excipients, in single or multiple doses. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques of formulation as are generally known to practitioners.

A pharmaceutical composition comprising an anti-IL-36R monoclonal antibody of the present description can be administered to a patient suffering from a neutrophilic dermatosis as described herein using standard administration techniques including oral, intravenous, intraperitoneal, subcutaneous, pulmonary, transdermal, intramuscular, intranasal, buccal, sublingual, or suppository administration.

The route of administration of an antibody of the present description may be oral, parenteral, by inhalation, or topical. Advantageously, the antibodies of the description can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are known in the art.

The pharmaceutical composition typically must be sterile and stable under the conditions of manufacture arid storage in the container provided, including e.g., a sealed vial or syringe. Therefore, pharmaceutical compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/mL or more) of antibody concentration. Dose may vary depending on the type and severity of the disease. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 mg; however, doses below or above this exemplary range are envisioned, especially considering the aforementioned factors.

The herein disclosed system 100 can automatically evaluate the severity of skin lesions in a patient with ND having visible signs and symptoms such as skin erythema, pustules and/or scaling to assist the treating physician to rapidly and conveniently form an objective assessment of the disease severity for the subject that is needed for an effective treatment of the patient. The treatment is advantageously applied when the patient has a severity score which corresponds at least to the severity level mild. That is, in the examples of FIG. 5, the drug administering threshold value is set to "2" in the case of the five-point scale example 112*a*, and is set to "1" in the case of the three-point scale example 112*b*.

Although neutrophilic dermatoses (NDs) are a heterogeneous group of conditions, they have common features and overlapping pathophysiology which involves the IL-36 pathway. While a neutrophilic dermatosis is associated primarily with cutaneous manifestations due to accumulation of neutrophils, IL-36 plays an important role in driving disease manifestation, particularly, in pustular NDs such as generalized pustular psoriasis (GPP), palmoplantar pustulosis (PPP), subcorneal pustulosis (Sneddon-Wilkinson), pustular psoriasis, acute generalized exanthematic pustulosis (AGEP), infantile acropustulosis (IA), Behcet disease, pustulosis, hyperostosis and osteitis (SAPHO) syndrome, bowel-associated dermatosis-arthritis syndrome (BADAS), neutrophilic dermatosis of the dorsal hands (NDDH), amicrobial pustulosis of the skinfolds (APF). Additionally, blocking IL-36 pathway may be beneficial in skin inflammation with papules, nodules and plaques such as acute febrile neutrophilic dermatoses (Sweet's syndrome), rheumatoid neutrophilic dermatitis (RND), neutrophilic eccrine hidradenitis (NEH), erythema elevatum diutinum (EED) and or with skin ulcerations such as pyoderma gangrenosum (PG). The IL-36 blockade is also beneficial in patients with ichthyosis (and its subtypes including netherton syndrome or NS).

Without wishing to be bound by this theory it is believed that anti-IL-36R antibodies bind to human IL-36R and thus interfere with the binding of IL-36 agonists, and in doing so block at least partially the signaling cascade from the IL-36R to inflammatory mediators involved in neutrophilic dermatoses. The anti-IL36R antibodies of the present description are disclosed herein an in, for example, in U.S. Pat. No. 9,023,995, the entire content of which is incorporated herein by reference.

In some embodiments, described and disclosed herein are anti-IL-36R antibodies, in particular humanized anti-IL-36R antibodies, and compositions and articles of manufacture comprising one or more anti-IL-36R antibody, in particular one or more humanized anti-IL-36R antibody of the present description. Also described are binding agents that include an antigen-binding fragment of an anti-IL-36 antibody, in particular a humanized anti-IL-36R antibody. In one embodiment, the anti-IL-36R antibody is Spesolimab (BI 655130).

The herein described approach can also be used in the context of modifying, discontinuing, or continuing the therapy of an individual receiving an anti-IL-36R antibody for treatment of ND. Based on the predicted severity score, the severity checker and antibody dosage modules can make a recommendation to modify, discontinue, or continue the treatment of the patient.

The herein described approach can also be used in the context of monitoring whether a patient receiving an anti-IL-36R antibody for treatment of ND is responsive to the treatment. Based on the predicted severity score, the severity checker can characterize the subject as responsive to the treatment with the anti-IL-36R antibody if the subject exhibits a decrease in the predicted severity score in comparison with an earlier predicted score.

Severity Scoring

The scoring of the erythema, pustules and scaling severities and calculation of a total neutrophilic dermatosis Area Severity Index (NDASI) and total neutrophilic dermatosis Global Assessment (NDGA) is further described in the following paragraphs, in the context of GPP, which are not intended to limit the scope of the description. The methods described below for GPPASI and GPPGA are equally applicable to scoring the severity in any ND condition (e.g., PPP) which has skin manifestation including erythema, pustules and/or scaling. Such scoring methods can be used for example for determining the ground truth for the training images where the scoring is performed manually.

Components of ND or GPP/PPP severity scores are: Erythema, Pustules, Scaling.

The severity of each component for later calculating the total Generalized Pustular Psoriasis Area Severity Index (GPPASI) and total Generalized Pustular Psoriasis Physician Global Assessment (GPPGA) are typically scored on a five-point scale: 0=clear 1=almost clear 2=mild 3=moderate 4=severe. Other scales are possible (cf. FIG. 5)

For GPPASI, typically each component is scored separately for each body region. For GPPGA, each component is typically scored either separately for each lesion or for all lesions. In cases where one lesion is identified and being scored, for calculating the total GPPGA, the sum of the severity scores for erythema, pustules and scaling is obtained and then the result is divided by three. In cases where more than one lesion is being scored for calculating the total GPPGA, the sum of the means, medians or maximums of the severity scores for erythema, pustules and scaling is obtained and then the result is divided by three.

For example for patients with light color skin (e.g., Whites, Asians), an erythema severity score of zero denotes a skin lesion or area with normal or post-inflammatory hyperpigmentation, an erythema severity score of one denotes a skin lesion or area with faint, diffuse pink or slight red color, an erythema severity score of two denotes a skin lesion or area with light red color, an erythema severity score of three denotes a skin lesion or area with bright red color, and an erythema severity score of four denotes a skin lesion or area with deep fiery red (see FIG. 11A). Further, a pustules severity score of zero denotes a skin lesion or area with no visible pustules, a pustules severity score of one denotes a skin lesion or area with low density occasional small discrete pustules (non-coalescent), a pustules severity of two denotes a skin lesion or area with moderate density grouped discrete small pustulates (non-coalescent), a pustules severity score of three denotes a skin lesion or area with high density pustules with some coalescence, and a pustules severity score of four denotes a skin lesion or area with very high density pustules with pustular lakes (see FIG. 11B). Furthermore, a scaling severity score of zero denotes a skin lesion or area with no scaling or crusting, a scaling severity score of one denotes a skin lesion or area with superficial focal scaling or crusting restricted to periphery of lesions, a scaling severity of two denotes a skin lesion or area with predominantly fine scaling or crusting, a scaling severity score of three denotes a skin lesion or area with moderate scaling or crusting covering most or all lesions, and a scaling severity score of four denotes a skin lesion or area with severe scaling or crusting covering most or all lesions (see FIG. 11C).

As described above, the severity of each of erythema, pustules and/or scaling on a skin area or lesion of a subject with ND can be scored by computer vision using an appropriate AI (artificial intelligence) algorithm which has been trained accordingly. Examples of such algorithms have been mentioned above. For example, a computer-implemented method according to the present description scores a digital image with ND lesion(s) for erythema, pustules and/or scaling severity by classifying the digital image in accordance with a training image dataset. The training image dataset contains digital images of skin lesions in which the severity of erythema, pustules and/or scaling are previously annotated or scored by expert dermatologists. In another example, scoring of a digital image with ND lesion(s) for erythema, pustules and/or scaling severity can be achieved by analyzing the level, intensity and/or the extent by which the skin has turned red (in case of erythema) or by counting the pustules, measuring their sizes, analyzing their colors and/or assessing how scatter or dense they appear in a given skin area (in case of pustules) or by outlining the edges of the scaling, and/or measuring their levels in terms of fineness or crustiness (in case of scaling).

Calculation of GPPASI

Body region factors: Head=0.1×, Upper limb=0.2×, Trunk=0.3×, Lower limb=0.4×.

Body region area score: 0=0% (no involvement), 1=>0-<10% involvement, 2=10-<30%, 3=30-<50%, 4=50-<70%, 5=70-<90%, 6=90-100%.

Individual score per body region=Body region factor× Body region area score*×Sum of component severity scores in body region (* Body region area score is the area affected by erythema and/or pustules and/or scaling; not assessed for each component separately).

Total GPPASI score=Sum of individual scores from all body regions.

Calculation of GPPGA

Individual component scores: Grade the severity of each component (erythema, pustules, and scaling) separately, for all lesions, using the severity scale (a five-point severity scale) of zero to four, with zero for clear, one for almost clear, two for mild, three for moderate and four for severe as shown in FIGS. 11A to 11C.

Composite mean score: Calculate the mean of individual component scores:

$$\frac{\text{Erythema} + \text{Pustules} + \text{Scaling}}{3}.$$

Total GPPGA scores:

0=If mean=0 for all three components

1=If 0<mean<1.5

2=If 1.5≤mean<2.5

3=If 2.5≤mean<3.5

4=If mean≥3.5

The description is further described in the following examples, which are not intended to limit the scope of the description.

Figure 12:
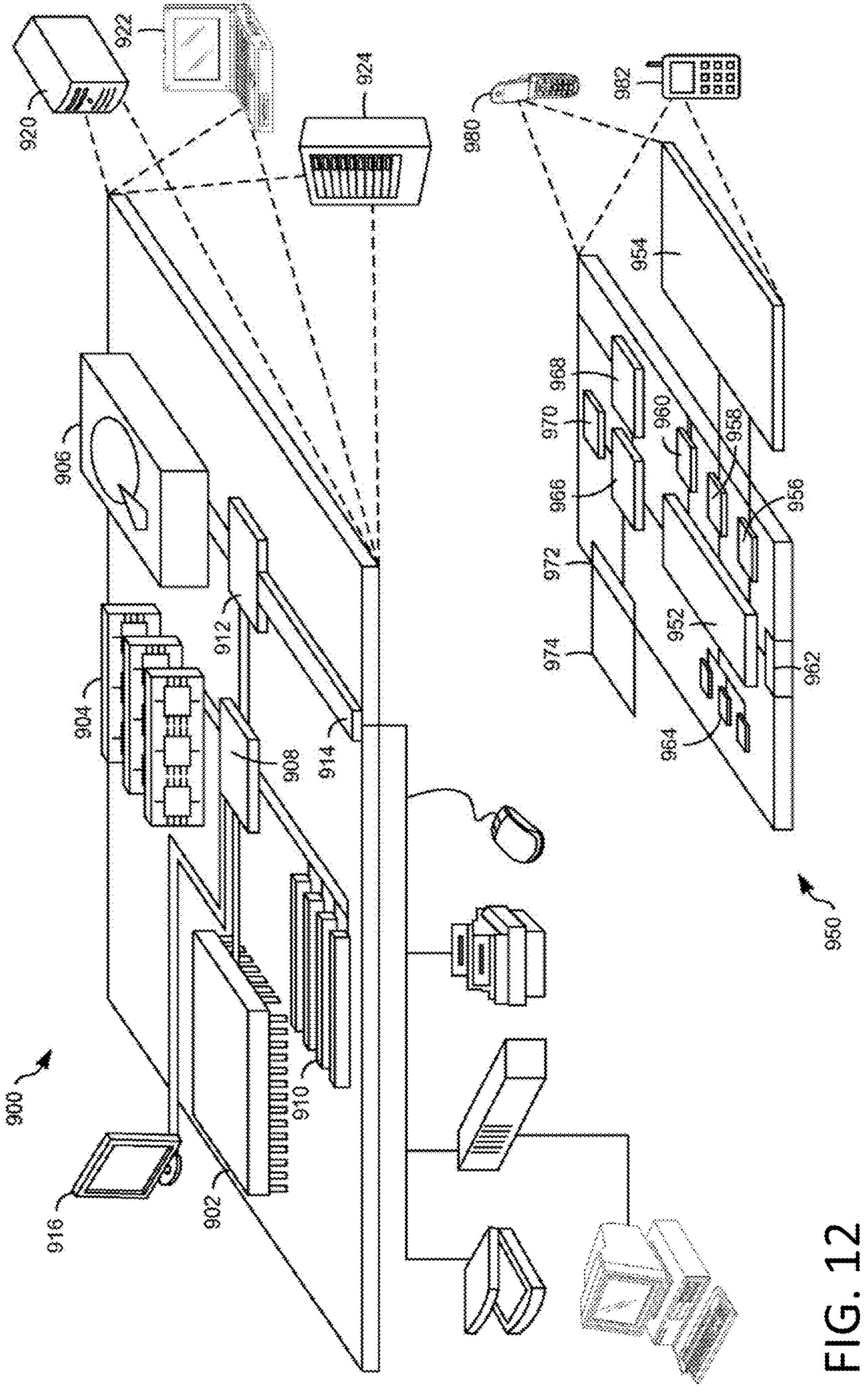
FIG. 12 is a diagram that shows an example of a generic computer device and a generic mobile computer device, which may be used with the techniques described herein.

FIG. 12 is a diagram that shows an example of a generic computer device 900 and a generic mobile computer device 950, which may be used with the techniques described here. Computing device 900 is intended to represent various forms of digital computers, such as laptops, desktops, workstations, personal digital assistants, servers, blade servers, mainframes, and other appropriate computers. Generic computer device 900 may correspond to the computer system 100 of FIG. 1. Computing device 950 is intended to represent various forms of mobile devices, such as personal digital assistants, cellular telephones, smart phones, and other similar computing devices. For example, computing device 950 may be used as a GUI frontend for a user to interact with the computer device 900, for example to receive from the computer device 900, the predicted severity score values and recommended dosage information, and/or to input certain data into the computer device, such as for example a corrected dosage to overwrite the recommended dosage. The components shown here, their connections and relationships, and their functions, are meant to be exemplary only, and are not meant to limit implementations of the descriptions and/or claimed in this document.

Computing device 900 includes a processor 902 (e.g., CPU, GPU), memory 904, a storage device 906, a high-speed interface 908 connecting to memory 904 and high-speed expansion ports 910, and a low-speed interface 912 connecting to low-speed bus 914 and storage device 906.

Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high-speed interface 908. In other implementations, multiple processing units and/or multiple buses may be used, as appropriate, along with multiple memories and types of memory. Also, multiple computing devices 900 may be connected, with each device providing portions of the necessary operations (e.g., as a server bank, a group of blade servers, or a processing device).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high-speed controller 908 manages bandwidth-intensive operations for the computing device 900, while the low-speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processing units. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the description.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The invention claimed is:

1. A computer-implemented method for predicting severity of a palmoplantar pustulosis condition of a patient using a deep neural network model, comprising:

receiving a test input digital image showing skin areas of the patient wherein the test input digital image comprises a grid with at least one pair of tiles, with a first tile showing a skin area of a front of a characteristic body part of the patient, and a second tile showing a skin area of a back of the characteristic body part of the patient, the characteristic body part being selected from: left and right palm, left and right sole, wherein at least one of the skin areas exhibits at least one of erythema, pustules and scaling; and predicting a total palmoplantar pustulosis global assessment (PPPGA) score for the patient, wherein predicting comprises applying the deep neural network model to the test input, wherein the deep neural network model has been trained with a training data set comprising a plurality of training images having a same structure as the test input and being captured from a plurality of test patients selected in accordance with predefined inclusion/exclusion criteria ensuring that the plurality of test patients have a generalized pustular psoriasis history without conflicting diseases, wherein the training data set comprises multiple training images of each test patient captured at different time points during a predefined minimum time interval, and each training image being annotated with one or more severity scores associated with erythema, pustules and scaling as a ground truth reflecting the severity of the palmoplantar pustulosis condition of a respective training patient at a timepoint a respective training image was captured.

2. A computer-implemented method for predicting severity of a generalized pustular psoriasis condition of a patient using a deep neural network model, comprising:

receiving a test input digital image showing skin areas of the patient wherein the test input digital image comprises a grid with at least one pair of tiles, with a first tile showing a skin area of a front of a characteristic body part of the patient, and a second tile showing a skin area of a back of the characteristic body part of the patient, the characteristic body part being selected from: trunk, left and right lower limb, left and right upper limb, wherein at least one of the skin areas exhibits at least one of erythema, pustules and scaling; and predicting a total Generalized Pustular Psoriasis Physician Global Assessment (GPPGA) score for the patient, wherein predicting comprises applying the deep neural network model to the test input, wherein the deep neural network model has been trained with a training data set comprising a plurality of training images having a same structure as the test input and being captured from a plurality of test patients selected in accordance with predefined inclusion/exclusion criteria ensuring that the plurality of test patients have a generalized pustular psoriasis history without conflicting diseases, wherein the training data set comprises multiple training images of each test patient captured at different time points during a predefined minimum time interval, and each training image being annotated with one or more severity scores associated with erythema, pustules and scaling as a ground truth reflecting the severity of the generalized pustular psoriasis condition of the respective training patient at a timepoint the training image was captured.

3. The method of claim 1 or 2, wherein each training image is annotated with one of at least three severity score values covering a severity range from clear to severe, the annotated severity score value reflecting an average of individual erythema, pustules, and scaling severity scores for the respective training image; and wherein the trained deep neural network model provides a single severity score value as output for the test input of said patient.

4. The method of claim 3, wherein the severity range includes the following score values for severity levels: clear, almost clear, mild, moderate, and severe.

5. The method of claim 1 or 2, wherein each training image is annotated with individual erythema, pustules and scaling severity score values, wherein each individual severity score value is one of at least three severity score values covering a severity range from clear to severe for the respective erythema, pustules and scaling severity on the training image; and wherein the trained deep neural network model provides individual severity score values for each of erythema, pustules and scaling severity as outputs; and wherein a single severity score for the test input of said patient is determined based on averaging the determined individual severity score values.

6. The method of claim 1 or 2, wherein feature sets of clinical tabular data of the patient are combined with features extracted from respective digital images of the patient for the severity prediction of said patient, wherein a particular feature set of clinical tabular data and a respective digital image are associated with the same severity of the patient's condition.

7. The method of claim 6, wherein clinical tabular data features are normalized and concatenated to the respective features extracted from convolutional layers of the deep neural network, and a concatenated feature set is used as input layer of classification layers of the deep neural network model, wherein the deep neural network has been trained with respective enhanced training data comprising the plurality of training images and associated feature sets of clinical tabular data features.

8. The method of claim 6, wherein a clinical data classifier has been trained on clinical tabular data features associated with the respective training images of the deep neural network model using a same ground truth, the training using Ensemble Learning for the clinical data classifier and the deep neural network, the method further comprising: combining the output of the deep neural network model and the output of the clinical data classifier into a single severity score.

9. The method of claim 1 or 2, wherein the deep neural network model implements any of the following algorithms: Convolutional Neural Network selected from ResNet, EfficientNet or ConvNeXT architectures; Vision Transformer; and combination network with convolutional layers and attention layers.

10. The method of claim 1 or 2, further comprising:

comparing a predicted severity score with a predefined drug administering threshold;

if the predicted severity score is equal to or greater than the predefined drug administering threshold, determining a dosage recommendation based on a pharmaceutically effective amount of an anti-interleukin-36 receptor antibody; and administering to the patient the recommended dosage of the anti-interleukin-36 receptor antibody for treatment of the palmoplantar pustulosis.

11. A computer program product for predicting severity of a palmoplantar pustulosis condition or a generalized pustular psoriasis condition of a patient, the computer program product being tangibly embodied on a non-transitory computer-readable storage medium, wherein the computer program product, when loaded into a memory of a computing device and executed by at least one processor of the computing device, causes the at least one processor to execute the steps of the computer-implemented methods according to claim 1 or 2.

12. A computer system for predicting severity of a palmoplantar pustulosis condition and/or a generalized pustular psoriasis condition of a patient using one or more respectively trained deep neural network models, the system comprising:

an interface configured to receive a test input digital image with skin areas of the patient wherein the test input digital image comprises a grid with at least one pair of tiles, with a first tile showing a skin area of a front of a characteristic body part of the patient, and a second tile showing a skin area of a back of the characteristic body part of the patient, wherein at least one of the skin areas exhibits at least one of erythema, pustules and scaling on the skin, wherein, in case the patient is suffering from palmoplantar pustulosis, the characteristic body part being selected from: left and right palm, left and right sole, and wherein, in case the patient is suffering from generalized pustular psoriasis, the characteristic body part being selected from: trunk, left and right lower limb, left and right upper limb; and a predictor module configured to predict a total palmoplantar pustulosis global assessment score and/or a total Generalized Pustular Psoriasis Physician Global Assessment score for the patient, wherein the predictor applies the one or more respectively trained deep neural network models to the test input, wherein the one or more deep neural network models are trained with a training data set comprising a plurality of training images having a same structure as the test input and being captured from a plurality of test patients selected in accordance with predefined inclusion/exclusion criteria ensuring that the training patients have, respectively, a palmoplantar pustulosis history and/or generalized pustular psoriasis history without conflicting diseases, wherein the training data set comprises multiple training images of each test patient captured at different time points during a predefined minimum time interval, and each training image being annotated with one or more severity scores associated with erythema, pustules and scaling as a ground truth reflecting respectively the severity of the palmoplantar pustulosis condition and/or the generalized pustular psoriasis condition of the respective training patient at a timepoint the training image was captured.

13. The system of claim 12, wherein the one or more deep neural network models implement any of the following algorithms: Convolutional Neural Network selected from ResNet, EfficientNet or ConvNeXT architectures; Vision Transformer; and combination network with convolutional layers and attention layers.

14. The system of claim 13, further comprising a severity checker module configured to compare a predicted severity score with a predefined drug administering threshold, wherein the predicted severity score has one of at least three severity score values covering a severity range from clear to severe, and, if the predicted severity score is equal to or greater than the predefined drug administering threshold, further configured to assign the patient as a candidate for treatment with an anti-interleukin-36 receptor antibody.

15. The system of claim 14, further comprising:

an antibody dosage module configured to determine for a candidate for treatment, based on the predicted severity score, a dosage recommendation based on a pharmaceutically effective amount of the anti-interleukin-36 receptor antibody suitable for treatment of the palmoplantar pustulosis condition and/or the generalized pustular psoriasis condition of the candidate, and to provide corresponding dosage instructions to a drug administering entity.

16. The system of claim 14, wherein the anti-interleukin-36 receptor antibody comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3); or VII. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 141 (H-CDR1); the amino acid sequence of SEQ ID NO: 62, 108, 109, 110, 111 or 142 (H-CDR2); the amino acid sequence of SEQ ID NO: 72 (H-CDR3).

17. The system of claim 14, wherein the anti-interleukin-36 receptor antibody comprises:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

18. The system of claim 14, wherein the anti-interleukin-36 receptor antibody comprises:

i. a light chain comprising the amino acid sequence of SEQ ID NO: 115; and a heavy chain comprising the amino acid sequence of SEQ ID NO: 125; or ii. a light chain comprising the amino acid sequence of SEQ ID NO: 115; and a heavy chain comprising the amino acid sequence of SEQ ID NO: 126; or iii. a light chain comprising the amino acid sequence of SEQ ID NO: 115; and a heavy chain comprising the amino acid sequence of SEQ ID NO: 127; or iv. a light chain comprising the amino acid sequence of SEQ ID NO: 118; and a heavy chain comprising the amino acid sequence of SEQ ID NO: 125; or v. a light chain comprising the amino acid sequence of SEQ ID NO: 118; and a heavy chain comprising the amino acid sequence of SEQ ID NO: 126; or vi. a light chain comprising the amino acid sequence of SEQ ID NO: 118; and a heavy chain comprising the amino acid sequence of SEQ ID NO: 127; or vii. a light chain comprising the amino acid sequence of SEQ ID NO: 123; and a heavy chain comprising the amino acid sequence of SEQ ID NO: 138; or viii. a light chain comprising the amino acid sequence of SEQ ID NO: 123; and a heavy chain comprising the amino acid sequence of SEQ ID NO: 139; or ix. a light chain comprising the amino acid sequence of SEQ ID NO: 124; and a heavy chain comprising the amino acid sequence of SEQ ID NO: 138.

19. The system of claim 14 wherein the anti-interleukin-36 receptor antibody is Spesolimab.

20. The system of claim 14 wherein a therapeutic effective amount of the anti-interleukin-36 receptor antibody is in the range of 0.001 to about 1200 mg.

21. The system of claim 12, wherein the predictor module is configured to combine feature sets of clinical tabular data of the patient with features extracted from respective digital images of the patient for the severity prediction of said patient, wherein a particular feature set of clinical tabular data and a respective digital image are associated with the same severity of the patient's condition.

22. The system of claim 12, wherein the predictor module is further configured to normalize clinical tabular data features and concatenate the normalized features to the respective features extracted from convolutional layers of the deep neural network, and wherein the concatenated feature set is used as input layer of classification layers of the deep neural network model, wherein the deep neural network has been trained with respective enhanced training data comprising the plurality of training images and associated feature sets of clinical tabular data features.

23. The system of claim 12, wherein the predictor module further comprises a clinical data classifier that has been trained on clinical tabular data features associated with the respective training images of the deep neural network model using the same ground truth, the training using Ensemble Learning for the clinical data classifier and the deep neural network, and wherein the predictor is further configured to combine the output of the deep neural network model and the output of the clinical data classifier into a single severity score.

* * * * *